(12) United States Patent
Yamamoto et al.

(10) Patent No.: US 6,562,599 B1
(45) Date of Patent: May 13, 2003

(54) SINGLE-STRANDED ANTIBODY AGAINST HEPATITIS B VIRUS CORE PROTEIN, GENE THEREOF, AND THERAPEUTIC AGENT FOR HEPATITIS B CONTAINING THESE

(75) Inventors: Masato Yamamoto, Hoover, AL (US); Norio Hayashi, Kawanishi (JP); Hiroko Yamamoto, Higashiosaka (JP); Naoki Tohdoh, Kobe (JP)

(73) Assignee: Sumitomo Pharmaceuticals Company, Limited, Osaka-fu (JP)

( * ) Notice: Subject to any disclaimer, the term of this patent is extended or adjusted under 35 U.S.C. 154(b) by 0 days.

(21) Appl. No.: 09/486,814

(22) PCT Filed: Sep. 2, 1998

(86) PCT No.: PCT/JP98/03921

§ 371 (c)(1),
(2), (4) Date: Apr. 27, 2000

(87) PCT Pub. No.: WO99/11792

PCT Pub. Date: Mar. 11, 1999

(30) Foreign Application Priority Data

Sep. 2, 1997 (JP) .............................................. 9-237054

(51) Int. Cl.[7] ................................................ C12P 21/08
(52) U.S. Cl. ................ 435/69.6; 536/23.53; 435/320.1; 435/173.3; 514/44
(58) Field of Search ..................... 536/23.53; 435/173.3, 435/69.1, 69.6, 320.1; 514/44

(56) References Cited

FOREIGN PATENT DOCUMENTS

| WO | 92 01047 | 1/1992 |
|----|----------|--------|
| WO | 94 15642 | 7/1994 |
| WO | 95 25167 | 9/1995 |
| WO | 95 33832 | 12/1995 |

OTHER PUBLICATIONS

Yamamoto et al., Intracellular Single–Chain Antibody Against Hepatitis B Virus Core Protein Inhibits the Replication of Hepatitis B Virus in Cultured Cells. Hepatology 30(1):300–307, 1999.*

M. Yamamoto et al., "Single–Chain Antibody Against Hepatitis B Virus Core Antigen Inhibited Hepaitis B Virus Replication in the Cells", Program and Abstracts from the 1st Annual Meeting of American Society of Gene Therapy, May 28–31, 1998, Seattle, Washington.

M. Yamamoto et al., "Single–Chain Antibody Against Hepatitis B Virus Core Antigen Inhibited Hepaitis B Virus Replication in the Cells", Program and Abstracts from the Fourth Annual Meeting of The Japan Society of Gene Therapy, Jul. 4–5, 1998, Bunkyo–ku, Japan.

John McCafferty et al., "Phage antibodies: filamentous phage displaying antibody variable domains", Nature, vol. 348, Dec. 6, 1990, pp. 552–554.

James D. Marks et al., "By–passing Immunization Human Antibodies from V–gene Libraries Displayed on Phage", J. Mol. Biol., (1991), pp. 581–597.

Canaán–Hayden et al., "Purification and Application of a Single–Chain Fv Antibody Fragment Specific to Hepatitis Virus Surface Antigen", BioTechniques, vol. 19, (Oct. 1995), pp. 606–614.

Pnina Levy–Mintz et al., "Intracellular Expression of Single–Chain Variable Fragments To Inhibit Early Stages of the Viral Life Cycle by Targeting Human Immunodeficiency Virus Type 1 Integrase", Journal of Virology, Dec. 1996, pp. 8821–8832.

Yong Wu et al., "Binding of Intracellular Anti–Rev Single Chain Variable Fragments to Different Epitopes of Human Immunodeficiency Virus Type 1 Rev: Variations in Viral Inhibition", Journal of Virology, May 1996, pp. 3290–3297.

Abner M. Mhashikar et al., "Inhibition of HIV–1 Tat–mediated LTR transactivation and HIV–1 infection by anti–Tat single chain intrabodies", The EMBO Journal, vol. 14, No. 7, pp. 1542–1551, 1995.

Russell C. Hirsch et al., "Polymerase gene products of hepatitis B viruses are required for genomic RNA packaging as well as for reverse transcription", Nature, vol. 344, Apr. 5, 1990, pp. 552–555.

Joel Lavine et al., "A System for Studying the Selective Encapsidation of Hepadnavirus RNA", Journal of Virology, Oct. 1989, pp. 4257–4263.

"Variable Region Sequence Modulates Periplasmic Export of a Single–Chain Fv Antibody Fragment in *Escherichia coli*", BioTechniques, vol. 18, No. 5, 1995, pp. 832–841.

* cited by examiner

*Primary Examiner*—Donna C Wortman
(74) *Attorney, Agent, or Firm*—Birch, Stewart, Kolasch & Birch, LLP

(57) ABSTRACT

A DNA characterized by coding for a single-stranded antibody capable of binding to a hepatitis B virus core protein: a single-stranded antibody coding for the DNA: a therapeutic agent for hepatitis B comprising the single-stranded antibody as the active ingredient; and a gene therapeutic agent containing the DNA as the active ingredient.

6 Claims, 12 Drawing Sheets

SEQUENCE LISTING

```
<160> NUMBER OF SEQ ID NOS: 14

<210> SEQ ID NO 1
<211> LENGTH: 894
<212> TYPE: DNA
<213> ORGANISM: Mus sp., strain: Balb/c, tissue: spleen
<220> FEATURE:
```

```
<223> OTHER INFORMATION: Clone: pZeoSV1C9
<220> FEATURE:
<221> NAME/KEY: CDS
<222> LOCATION: (1)..(891)
<223> OTHER INFORMATION: Identification Method: E
<220> FEATURE:
<221> NAME/KEY: misc_feature
<222> LOCATION: (1)..(111)
<223> OTHER INFORMATION: Encoding PRE-HV sequence
<220> FEATURE:
<221> NAME/KEY: misc_feature
<222> LOCATION: (436)..(528)
<223> OTHER INFORMATION: Encoding a linker sequence
<220> FEATURE:
<221> NAME/KEY: misc_feature
<222> LOCATION: (838)..(891)
<223> OTHER INFORMATION: Encoding a TAIL sequence
<220> FEATURE:
<221> NAME/KEY: misc_feature
<222> LOCATION: (1)..(894)
<223> OTHER INFORMATION: strandedness:  double-stranded

<400> SEQUENCE: 1 atg acc atg att acg cca agc ttt gga gcc ttt ttt ttg gag att ttc      48
Met Thr Met Ile Thr Pro Ser Phe Gly Ala Phe Phe Leu Glu Ile Phe
 1               5                  10                  15 aac gtg aaa aaa tta tta ttc gca att cct tta gtt gtt cct ttc tat      96
Asn Val Lys Lys Leu Leu Phe Ala Ile Pro Leu Val Val Pro Phe Tyr
             20                  25                  30 gcg gcc cag ccg gcc atg gcc cag gtg aag ctg cag gag tca gga cct     144
Ala Ala Gln Pro Ala Met Ala Gln Val Lys Leu Gln Glu Ser Gly Pro
         35                  40                  45 gag ctg gag aag cct ggc gct tca gtg aag ata tcc tgc aag gct tct     192
Glu Leu Glu Lys Pro Gly Ala Ser Val Lys Ile Ser Cys Lys Ala Ser
     50                  55                  60 ggt tac tca ttc act ggc tac aac atg aag tgg gtg aaa cag agc aat     240
Gly Tyr Ser Phe Thr Gly Tyr Asn Met Lys Trp Val Lys Gln Ser Asn
 65                  70                  75                  80 gga aag agc ctt gag tgg att gga tat att tat cct tac aat ggt ggt     288
Gly Lys Ser Leu Glu Trp Ile Gly Tyr Ile Tyr Pro Tyr Asn Gly Gly
                 85                  90                  95 act ggc tac aac cag aag ttc aag agc aag gcc aca ttg act gta gac     336
Thr Gly Tyr Asn Gln Lys Phe Lys Ser Lys Ala Thr Leu Thr Val Asp
            100                 105                 110 aaa tcc tcc agc aca gcc tac atg caa ctg agc agc ctg aca tct gag     384
Lys Ser Ser Ser Thr Ala Tyr Met Gln Leu Ser Ser Leu Thr Ser Glu
        115                 120                 125 gac tct gca gtc tat tac tgt gca aga ctg gga ctt gac tac tgg ggc     432
Asp Ser Ala Val Tyr Tyr Cys Ala Arg Leu Gly Leu Asp Tyr Trp Gly
    130                 135                 140 caa ggg acc acg gtc acc gtc tcc tca ggt gga ggc ggt tca ggc gga     480
Gln Gly Thr Thr Val Thr Val Ser Ser Gly Gly Gly Gly Ser Gly Gly
145                 150                 155                 160 ggt ggc tct ggc ggt ggc gga tcg gac atc gag ctc act cag tct cca     528
Gly Gly Ser Gly Gly Gly Gly Ser Asp Ile Glu Leu Thr Gln Ser Pro
                165                 170                 175 acc acc atg gct gca tct ccc ggg gag aag atc act atc acc tgc agt     576
Thr Thr Met Ala Ala Ser Pro Gly Glu Lys Ile Thr Ile Thr Cys Ser
            180                 185                 190 gcc agc tca agt ata agt tcc aat tac ttg cat tgg tat cag cag aag     624
Ala Ser Ser Ser Ile Ser Ser Asn Tyr Leu His Trp Tyr Gln Gln Lys
        195                 200                 205 cca gga ttc tcc cct aaa ctc ttg att tat agg aca tcc aat ctg gct     672
Pro Gly Phe Ser Pro Lys Leu Leu Ile Tyr Arg Thr Ser Asn Leu Ala
    210                 215                 220
```

```
tct gga atc cca gct cgc ttc agt ggc agt ggg tct ggg acc tct tac    720
Ser Gly Ile Pro Ala Arg Phe Ser Gly Ser Gly Ser Gly Thr Ser Tyr
225                 230                 235                 240 tct ctc aca att ggc acc atg gag gct gaa gat gtt gcc act tac tac    768
Ser Leu Thr Ile Gly Thr Met Glu Ala Glu Asp Val Ala Thr Tyr Tyr
                245                 250                 255 tgc cag cag ggt agt agt ata cca cgc ata ttc acg ttc ggt gct ggg    816
Cys Gln Gln Gly Ser Ser Ile Pro Arg Ile Phe Thr Phe Gly Ala Gly
            260                 265                 270 aca aag ttg gaa ata aaa cgg gcg gcc gca ggt gcg ccg gtg ccg tat    864
Thr Lys Leu Glu Ile Lys Arg Ala Ala Ala Gly Ala Pro Val Pro Tyr
        275                 280                 285 ccg gat ccg ctg gaa ccg cgt gcc gca tag                            894
Pro Asp Pro Leu Glu Pro Arg Ala Ala
    290                 295

<210> SEQ ID NO 2
<211> LENGTH: 297
<212> TYPE: PRT
<213> ORGANISM: Mus sp., strain: Balb/c, tissue: spleen
<220> FEATURE:
<221> NAME/KEY: PEPTIDE
<222> LOCATION: (1)..(145)
<223> OTHER INFORMATION: Identification Method: P
<220> FEATURE:
<221> NAME/KEY: PEPTIDE
<222> LOCATION: (177)..(279)
<223> OTHER INFORMATION: Identification Method: P

<400> SEQUENCE: 2

Met Thr Met Ile Thr Pro Ser Phe Gly Ala Phe Phe Leu Glu Ile Phe
1               5                   10                  15

Asn Val Lys Lys Leu Leu Phe Ala Ile Pro Leu Val Val Pro Phe Tyr
            20                  25                  30

Ala Ala Gln Pro Ala Met Ala Gln Val Lys Leu Gln Glu Ser Gly Pro
        35                  40                  45

Glu Leu Glu Lys Pro Gly Ala Ser Val Lys Ile Ser Cys Lys Ala Ser
    50                  55                  60

Gly Tyr Ser Phe Thr Gly Tyr Asn Met Lys Trp Val Lys Gln Ser Asn
65                  70                  75                  80

Gly Lys Ser Leu Glu Trp Ile Gly Tyr Ile Tyr Pro Tyr Asn Gly Gly
                85                  90                  95

Thr Gly Tyr Asn Gln Lys Phe Lys Ser Lys Ala Thr Leu Thr Val Asp
            100                 105                 110

Lys Ser Ser Ser Thr Ala Tyr Met Gln Leu Ser Ser Leu Thr Ser Glu
        115                 120                 125

Asp Ser Ala Val Tyr Tyr Cys Ala Arg Leu Gly Leu Asp Tyr Trp Gly
    130                 135                 140

Gln Gly Thr Thr Val Thr Val Ser Ser Gly Gly Gly Gly Ser Gly Gly
145                 150                 155                 160

Gly Gly Ser Gly Gly Gly Gly Ser Asp Ile Glu Leu Thr Gln Ser Pro
                165                 170                 175

Thr Thr Met Ala Ala Ser Pro Gly Glu Lys Ile Thr Ile Thr Cys Ser
            180                 185                 190

Ala Ser Ser Ser Ile Ser Ser Asn Tyr Leu His Trp Tyr Gln Gln Lys
        195                 200                 205

Pro Gly Phe Ser Pro Lys Leu Leu Ile Tyr Arg Thr Ser Asn Leu Ala
    210                 215                 220
```

-continued

```
Ser Gly Ile Pro Ala Arg Phe Ser Gly Ser Gly Ser Gly Thr Ser Tyr
225                 230                 235                 240

Ser Leu Thr Ile Gly Thr Met Glu Ala Glu Asp Val Ala Thr Tyr Tyr
                245                 250                 255

Cys Gln Gln Gly Ser Ser Ile Pro Arg Ile Phe Thr Phe Gly Ala Gly
            260                 265                 270

Thr Lys Leu Glu Ile Lys Arg Ala Ala Gly Ala Pro Val Pro Tyr
        275                 280                 285

Pro Asp Pro Leu Glu Pro Arg Ala Ala
    290                 295
```

<210> SEQ ID NO 3
<211> LENGTH: 324
<212> TYPE: DNA
<213> ORGANISM: Mus sp., strain: Balb/c, tissue: spleen
<220> FEATURE:
<223> OTHER INFORMATION: Clone: pZeoSV1C9
<220> FEATURE:
<221> NAME/KEY: CDS
<222> LOCATION: (1)..(324)
<223> OTHER INFORMATION: Identification Method: E

<400> SEQUENCE: 3

```
atg gcc cag gtg aag ctg cag gag tca gga cct gag ctg gag aag cct      48
Met Ala Gln Val Lys Leu Gln Glu Ser Gly Pro Glu Leu Glu Lys Pro
  1               5                  10                  15 ggc gct tca gtg aag ata tcc tgc aag gct tct ggt tac tca ttc act      96
Gly Ala Ser Val Lys Ile Ser Cys Lys Ala Ser Gly Tyr Ser Phe Thr
             20                  25                  30 ggc tac aac atg aag tgg gtg aaa cag agc aat gga aag agc ctt gag     144
Gly Tyr Asn Met Lys Trp Val Lys Gln Ser Asn Gly Lys Ser Leu Glu
         35                  40                  45 tgg att gga tat att tat cct tac aat ggt ggt act ggc tac aac cag     192
Trp Ile Gly Tyr Ile Tyr Pro Tyr Asn Gly Gly Thr Gly Tyr Asn Gln
     50                  55                  60 aag ttc aag agc aag gcc aca ttg act gta gac aaa tcc tcc agc aca     240
Lys Phe Lys Ser Lys Ala Thr Leu Thr Val Asp Lys Ser Ser Ser Thr
 65                  70                  75                  80 gcc tac atg caa ctg agc agc ctg aca tct gag gac tct gca gtc tat     288
Ala Tyr Met Gln Leu Ser Ser Leu Thr Ser Glu Asp Ser Ala Val Tyr
                 85                  90                  95 tac tgt gca aga ctg gga ctt gac tac tgg ggc caa                     324
Tyr Cys Ala Arg Leu Gly Leu Asp Tyr Trp Gly Gln
            100                 105
```

<210> SEQ ID NO 4
<211> LENGTH: 108
<212> TYPE: PRT
<213> ORGANISM: Mus sp., strain: Balb/c, tissue: spleen
<220> FEATURE:
<221> NAME/KEY: PEPTIDE
<222> LOCATION: (1)..(108)
<223> OTHER INFORMATION: Identification Method: P

<400> SEQUENCE: 4

```
Met Ala Gln Val Lys Leu Gln Glu Ser Gly Pro Glu Leu Glu Lys Pro
  1               5                  10                  15

Gly Ala Ser Val Lys Ile Ser Cys Lys Ala Ser Gly Tyr Ser Phe Thr
             20                  25                  30

Gly Tyr Asn Met Lys Trp Val Lys Gln Ser Asn Gly Lys Ser Leu Glu
         35                  40                  45

Trp Ile Gly Tyr Ile Tyr Pro Tyr Asn Gly Gly Thr Gly Tyr Asn Gln
```

```
                50                  55                  60
Lys Phe Lys Ser Lys Ala Thr Leu Thr Val Asp Lys Ser Ser Thr
 65                  70                  75                  80

Ala Tyr Met Gln Leu Ser Ser Leu Thr Ser Glu Asp Ser Ala Val Tyr
                 85                  90                  95

Tyr Cys Ala Arg Leu Gly Leu Asp Tyr Trp Gly Gln
                100                 105
```

<210> SEQ ID NO 5
<211> LENGTH: 309
<212> TYPE: DNA
<213> ORGANISM: Mus sp., strain: Balb/c, tissue: spleen
<220> FEATURE:
<223> OTHER INFORMATION: Clone: pZeoSV1C9
<220> FEATURE:
<221> NAME/KEY: CDS
<222> LOCATION: (1)..(309)
<223> OTHER INFORMATION: Identification Method: E

<400> SEQUENCE: 5

```
acc acc atg gct gca tct ccc ggg gag aag atc act atc acc tgc agt      48
Thr Thr Met Ala Ala Ser Pro Gly Glu Lys Ile Thr Ile Thr Cys Ser
 1               5                  10                  15 gcc agc tca agt ata agt tcc aat tac ttg cat tgg tat cag cag aag      96
Ala Ser Ser Ser Ile Ser Ser Asn Tyr Leu His Trp Tyr Gln Gln Lys
             20                  25                  30 cca gga ttc tcc cct aaa ctc ttg att tat agg aca tcc aat ctg gct     144
Pro Gly Phe Ser Pro Lys Leu Leu Ile Tyr Arg Thr Ser Asn Leu Ala
         35                  40                  45 tct gga atc cca gct cgc ttc agt ggc agt ggg tct ggg acc tct tac     192
Ser Gly Ile Pro Ala Arg Phe Ser Gly Ser Gly Ser Gly Thr Ser Tyr
     50                  55                  60 tct ctc aca att ggc acc atg gag gct gaa gat gtt gcc act tac tac     240
Ser Leu Thr Ile Gly Thr Met Glu Ala Glu Asp Val Ala Thr Tyr Tyr
 65                  70                  75                  80 tgc cag cag ggt agt agt ata cca cgc ata ttc acg ttc ggt gct ggg     288
Cys Gln Gln Gly Ser Ser Ile Pro Arg Ile Phe Thr Phe Gly Ala Gly
                 85                  90                  95 aca aag ttg gaa ata aaa cgg                                         309
Thr Lys Leu Glu Ile Lys Arg
            100
```

<210> SEQ ID NO 6
<211> LENGTH: 103
<212> TYPE: PRT
<213> ORGANISM: Mus sp., strain: Balb/c, tissue: spleen
<220> FEATURE:
<221> NAME/KEY: PEPTIDE
<222> LOCATION: (1)..(103)
<223> OTHER INFORMATION: Identification Method: P

<400> SEQUENCE: 6

```
Thr Thr Met Ala Ala Ser Pro Gly Glu Lys Ile Thr Ile Thr Cys Ser
 1               5                  10                  15

Ala Ser Ser Ser Ile Ser Ser Asn Tyr Leu His Trp Tyr Gln Gln Lys
             20                  25                  30

Pro Gly Phe Ser Pro Lys Leu Leu Ile Tyr Arg Thr Ser Asn Leu Ala
         35                  40                  45

Ser Gly Ile Pro Ala Arg Phe Ser Gly Ser Gly Ser Gly Thr Ser Tyr
     50                  55                  60

Ser Leu Thr Ile Gly Thr Met Glu Ala Glu Asp Val Ala Thr Tyr Tyr
 65                  70                  75                  80
```

Cys Gln Gln Gly Ser Ser Ile Pro Arg Ile Phe Thr Phe Gly Ala Gly
                85                  90                  95

Thr Lys Leu Glu Ile Lys Arg
        100

<210> SEQ ID NO 7
<211> LENGTH: 111
<212> TYPE: DNA
<213> ORGANISM: Artificial Sequence
<220> FEATURE:
<223> OTHER INFORMATION: Description of Artificial Sequence: Targeted to
      Hepatitis B virus core antibody
<220> FEATURE:
<221> NAME/KEY: CDS
<222> LOCATION: (1)..(111)
<223> OTHER INFORMATION: Identification Method: P

<400> SEQUENCE: 7 atg acc atg att acg cca agc ttt gga gcc ttt ttt ttg gag att ttc        48
Met Thr Met Ile Thr Pro Ser Phe Gly Ala Phe Phe Leu Glu Ile Phe
  1               5                  10                  15 aac gtg aaa aaa tta tta ttc gca att cct tta gtt gtt cct ttc tat       96
Asn Val Lys Lys Leu Leu Phe Ala Ile Pro Leu Val Val Pro Phe Tyr
                20                  25                  30 gcg gcc cag ccg gcc                                                  111
Ala Ala Gln Pro Ala
        35

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Targeted to
      Hepatitis B virus core antibody

<400> SEQUENCE: 8

Met Thr Met Ile Thr Pro Ser Phe Gly Ala Phe Phe Leu Glu Ile Phe
  1               5                  10                  15

Asn Val Lys Lys Leu Leu Phe Ala Ile Pro Leu Val Val Pro Phe Tyr
                20                  25                  30

Ala Ala Gln Pro Ala
        35

<210> SEQ ID NO 9
<211> LENGTH: 93
<212> TYPE: DNA
<213> ORGANISM: Artificial Sequence
<220> FEATURE:
<223> OTHER INFORMATION: Description of Artificial Sequence: Targeted to
      Hepatitis B virus core antibody
<220> FEATURE:
<221> NAME/KEY: CDS
<222> LOCATION: (1)..(93)
<223> OTHER INFORMATION: Identification Method: P

<400> SEQUENCE: 9 ggg acc acg gtc acc gtc tcc tca ggt gga ggc ggt tca ggc gga ggt        48
Gly Thr Thr Val Thr Val Ser Ser Gly Gly Gly Gly Ser Gly Gly Gly
  1               5                  10                  15 ggc tct ggc ggt ggc gga tcg gac atc gag ctc act cag tct cca           93
Gly Ser Gly Gly Gly Gly Ser Asp Ile Glu Leu Thr Gln Ser Pro
                20                  25                  30

<210> SEQ ID NO 10

```
<211> LENGTH: 31
<212> TYPE: PRT
<213> ORGANISM: Artificial Sequence
<220> FEATURE:
<223> OTHER INFORMATION: Description of Artificial Sequence: Targeted to
      Hepatitis B virus core antibody

<400> SEQUENCE: 10

Gly Thr Thr Val Thr Val Ser Ser Gly Gly Gly Ser Gly Gly Gly
 1               5                  10                  15

Gly Ser Gly Gly Gly Gly Ser Asp Ile Glu Leu Thr Gln Ser Pro
            20                  25                  30

<210> SEQ ID NO 11
<211> LENGTH: 57
<212> TYPE: DNA
<213> ORGANISM: Artificial Sequence
<220> FEATURE:
<223> OTHER INFORMATION: Description of Artificial Sequence: Targeted to
      Hepatitis B virus core antibody
<220> FEATURE:
<221> NAME/KEY: CDS
<222> LOCATION: (1)..(54)
<223> OTHER INFORMATION: Identification Method: P

<400> SEQUENCE: 11 gcg gcc gca ggt gcg ccg gtg ccg tat ccg gat ccg ctg gaa ccg cgt      48
Ala Ala Ala Gly Ala Pro Val Pro Tyr Pro Asp Pro Leu Glu Pro Arg
 1               5                  10                  15 gcc gca tag                                                          57
Ala Ala

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Targeted to
      Hepatitis B virus

<400> SEQUENCE: 12

Ala Ala Ala Gly Ala Pro Val Pro Tyr Pro Asp Pro Leu Glu Pro Arg
 1               5                  10                  15

Ala Ala

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: synthetic
      DNA primer targeted to Hepatitis B virus core protein antigen

<400> SEQUENCE: 13
gggctagcgt gtggaattgt gagcggataa ca                                  32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: synthetic
      DNA primer targeted to Hepatitis B virus core protein antigen

<400> SEQUENCE: 14
ggctcgagca gccctcatag ttagcgtaac ga                                  32
```

SINGLE-STRANDED ANTIBODY AGAINST HEPATITIS B VIRUS CORE PROTEIN, GENE THEREOF, AND THERAPEUTIC AGENT FOR HEPATITIS B CONTAINING THESE

This application is the national phase under 35 U.S.C. §371 of PCT International Application No. PCT/JP98/03921 which has an International filing date of Sep. 2, 1998, which designated the United States of America.

TECHNICAL FIELD

The present invention relates to single-chain antibodies against hepatitis B virus core protein, genes thereof, and therapeutic agents for hepatitis B using the same. In particular, the present invention relates to single-chain antibodies characterized in that they inhibit DNA synthesis of hepatitis B virus by binding to the core protein of said virus, DNAs encoding said single-chain antibodies, vectors comprising said DNAs, transformants transformed with said vectors, a process for producing said single-chain antibodies, and therapeutic agents for hepatitis B using such single-chain antibodies or genes thereof.

BACKGROUND ART

In Japan, hepatitis B virus (hereinafter sometimes abbreviated as HBV) accounts for a large part of the etiology of chronic hepatitis, as well as hepatitis C virus. Although the proportion of the virus carriers tends to decrease as a result of the recent preventive treatment by vaccination, there still exists a substantial number of patients with chronic hepatitis B, and medical treatments for this disease is quite important in terms of prophylaxis of primary hepatic cancer.

As medical treatments for patients with chronic hepatitis B, those treatments that aim to exclude the virus by eliciting the host immunity, such as the interferon therapy, the steroid withdrawal therapy, and the propagermanium therapy, or the antiviral agent therapies (adenine arabinoside monophosphate, hereinafter sometimes abbreviated as ara-AMP), Lamivudine) are now being used. In the interferon therapy, however, a long-term clinical improvement cannot be observed, although a transient decrease in amount of serological markers of viral activities occurs. Likewise, although ara-AMP has been used with some effect, it is hard to say that the results are satisfactory at present. A treatment in which interferon and ara-AMP are combined and alternately administered exhibits neurotoxicity, and therefore has problems in its use. Furthermore, fulminant hepatitis B, which is one of the forms of acute hepatitis B, is a disease causing a high lethality, and there exist no effective therapeutic agents for this disease presently. Thus, although there is a strong need for developing an anti-hepatitis B virus therapy based on a different mechanism from those of conventional methods, no useful therapies have not yet been developed.

As one of antiviral therapies, there is a method using antibodies specific for viral antigens. Although a method that intracellularly expresses such an antibody may possibly inhibit only the target antigen without damaging the host cells by virtue of the high specificity of the antibody, when IgGs are administered from outside of the cells, they can not inhibit the functions of the viral antigens existing within the cells due to the low efficiency of uptake into the cells. Furthermore, when genes for the H and L strands of an anti-viral antigen-IgG are introduced into cells that are not natural antibody forming cells, the H and L strands expressed from the transgenes will not necessarily form disulfide bonds as efficient as in antibody producing cells to produce IgG in its active form.

On the other hand, a protein produced by expressing a contiguous sequence of cDNAs, in which one cDNA corresponding to the variable region derived from the L strand of an antibody (hereinafter sometimes abbreviated as $V_L$) and another cDNA corresponding to the variable region derived from the H strand of the antibody (hereinafter sometimes abbreviated as $V_H$) are connected together through an appropriate oligonucleotide linker encoding a highly flexible peptide sequence, can specifically bind to the antigen while taking a structure containing no disulfide bonds. Such proteins are called "single-chain antibodies", and characterized in that they do not require to be expressed in antibody producing cells in order to form their proper three-dimensional structures as in the above-mentioned IgG, and even when expressed in cells other than antibody producing cells, they have activity of specifically binding to the antigen (McCafferty J. et al., Nature (London), 348, 552–554 (1990); and Marks J. D. et al., J. Mol. Biol. 222, 581–597 (1991)).

As examples of researches on single-chain antibodies aiming at their application to diseases, for example, cancer, those studies may be mentioned in which (a) cDNAs for a single-chain antibody and for a physiologically active substance such as a toxin are ligated together and expressed with the expectation that they will attack and thereby reduce the target cells, or in which (b) the specific binding of the single-chain antibody to the antigen is expected in itself to produce a desired effect.

As specific examples of the above (a), studies have been reported on conjugates in which TGF-α or a toxin such as the diphtheria toxin is coupled to an anti-EGFR single-chain antibody (Schmidt M. and Wels W., Br. J. Cancer, 74, 853–862 (1996)), anti-erbB-2 single-chain antibody (Wels W. et al., Cancer Res., 52, 6310–6317 (1992); and Schmidt M. and Wels W., Br. J. Cancer, 74,853–862 (1996)), and anti-CD 40 single-chain antibody (Francesco J A. et al., Cancer Res., 55, 3099–3104 (1995)), or on conjugates in which a neurotoxin derived from eosinophil is coupled to an anti-transferrin receptor single-chain antibody (Newton D L. et al., J. Biol. Chem., 269, 26739–26745 (1994)). In these studies, conjugates between a toxin and a single-chain antibody were prepared and the single-chain antibodies were allowed to specifically bind, for example, to target cells with the expectation that only the target cells bound by the single-chain antibodies will be necrotized by the toxin.

As specific examples of the above (b), studies have been reported on single-chain antibodies against erbB-2 (Grim J. et al., Am. J. Respir. Cell. Mol. Biol., 15, 348–354 (1996); Jannot C. B. et al., Oncogene, 13, 275–282 (1996), EGFR (Jannot C B. et al., Oncogene, 13, 275–282 (1996)), and Ras (Werge T M. et al., FEBS Lett., 351, 393–396 (1994)). Furthermore, MMLV engineered so that it expresses an anti-MHC single-chain antibody on its surface has been used in an application for directly delivering it to MHC.

Examples of reported studies on single-chain antibodies against viruses aiming at their application to diseases are those studies against HIV (Wu Y. et al., J. Virol., 70, 3290–3297 (1996); Levy-Mintz P., J. Virol., 70, 8821–8832 (1996); Mhashilkar A M. et al., EMBO J., 14, 1542–1551 (1995)), Foot-and-mouth disease virus (Mason P. et al., Virology, 224, 548–554 (1996)), and Tick-borne fravivirus (Jiang W., J. Virol., 69, 1044–1049 (1995)). In these studies, the targets of single-chain antibodies against HIV are non-structural proteins such as Rev (Wu Y. et al., J. Virol., 70, 3290–3297 (1996)) and Tat (Mhashilkar A M. et al., *EMBO J.*, 14, 1542–1551 (1995)). Since Rev protein binds to HIV-1 mRNA containing RRE expressed in HIV-1 infected cells and promotes expression of gag, pol, and env gene, binding of a single-chain antibody to this protein can inactivate Rev, and thereby suppress propagation of the virus by reduced expression of gag, pol, and env gene.

Tat protein has a transactivator activity, and specific binding of a single-chain antibody to this protein inhibits this activity and thereby suppresses propagation of HIV. In the case of the single-chain antibody against Tick-borne fravivirus, of which target is a viral surface antigen, it has a neutralizing activity and its binding to the structural protein on the viral surface decreases the viral infection and the synthesis of viral proteins.

However, all the antigens to which these single-chain antibodies are targeted are nonstructural proteins or structural proteins on the viral surface. A drawback of viral surface antigens is that the target antigens are prone to undergo mutation due to strong immuno-pressure exerted thereon, and the specific binding of single-chain antibody is thereby disturbed. For example, there exists a region prone to undergo mutation, called hypervariable region, and the region may be a cause that inhibits the specific binding of the single-chain antibody. Likewise, non-structural proteins may undergo mutations, even though the frequency is lower than that of viral surface antigens, and therefore they have a drawback that the binding of single-chain antibody is thereby similarly disturbed.

On the other hand, the only known example of single-chain antibody against HBV is a single-chain antibody against a surface antigen of HBV (*Biotechniques* 18:832 (1995), WO95/33832). However, since this single-chain antibody is against a surface antigen as described above, it has a drawback that the specific binding is inhibited by mutations produced in the target antigen. Furthermore, the above single-chain antibody against HBV is produced merely for the purpose of applying it to purification or immunoassay of the antigen.

DISCLOSURE OF THE INVENTION

Thus, the present invention has been made in the light of the above conventional problems, and it aims to provide single-chain antibodies against hepatitis B virus core protein, genes thereof, and therapeutic agents for hepatitis B using the same. More particularly, the present invention aims to provide single-chain antibodies characterized in that they suppress DNA synthesis of said virus by binding to hepatitis B virus core protein, DNAs encoding said single-chain antibodies, vectors containing said DNAs, transformants transformed with said vectors, a process for producing the above single-chain antibodies, and therapeutic agents for hepatitis B using such single-chain antibodies or genes thereof.

By noting the fact that propagation of hepatitis B virus proceeds through a process characteristic of hepadnavirus, the present inventors have developed a novel method for suppressing propagation of hepatitis B virus as a means of solving the above-described problems.

It is known that replication of hepatitis B virus proceeds through a process as described below.

Within virions in the blood, the viral gene exists as a circular incompletely duplex DNA having about 10% single-stranded parts. After infection, when transferred into the nuclei, however, the single-stranded parts are repaired to give a closed circular double-stranded DNA, and the mRNAs for viral proteins and pregenome RNA are transcribed by cellular RNA polymerase from the four open reading frames. Among these substances, the pregenome RNA is packaged together with hepatitis B virus DNA polymerase and reverse transcriptase into the core particle consisting of the core protein, covered by coat protein after synthesis of the minus strand and partial synthesis of the plus strand in the core particle by reverse transcription, and the mature hepatitis B virions are then released out of the cells.

It is believed that the core protein plays an important role in the process of reverse transcription from the pregenome RNA and that the core protein is essential for the virus to have a structure capable of being packaged (Ganem, D., Hepadønaviridae and their replication, In "Fields Virology" (B. N. Fields, D. M. Knipe and P. M. Howley, Eds.-in-Chief) 3rd ed., 2703–2737 (1996), Lippincott-Raven Publishers, Philadelphia; Hirsh, R. et al., *Nature*, 344, 552–555 (1990); and Lavinem J. et al., *J. Virol.*, 63, 4257–4263 (1989)). It is therefore expected that if one can inhibit functions of the core protein, the viral maturation process subsequent to the reverse transcription, which occurs in the capsid, may be thereby suppressed.

Since the capsid exists in the cells, an agent inhibiting functions of the core protein has to exist within the cells. As methods for inhibiting functions of the core protein within the cells, those methods may be contemplated in which an anti-core protein antibody is intracellularly expressed or in which a mutant core protein is expressed.

The present inventors have immunized a mouse with hepatitis B virus core protein, purified RNA from the spleen, prepared cDNA fragments that encode polypeptides corresponding to $V_L$ and $V_H$ regions of an antibody against hepatitis B virus core protein by PCR method, and then obtained a single-chain antibody against the core protein (abbreviated as anti-core protein single-chain antibody) to complete the present invention.

In addition, the present inventors have introduced the above gene into a mammalian expression vector in order to express the anti-core protein single-chain antibody in human-derived cultured cells that persistently produce hepatitis B virus, and thereby succeeded in observing significant decrease in amount of replicative intermediate DNAs for hepatitis B virus, that is, suppression of propagation of hepatitis B virus, although the amount of mRNA for hepatitis B virus transcribed within the transformed cells was not affected when compared to that of mRNA in the negative control transformant. The present inventors have thus arrived at the present invention.

Accordingly, the gist of the present invention relates to:

(1) DNA characterized in that it encodes a single-chain antibody capable of binding to hepatitis B virus core protein;

(2) DNA of the above (1) which comprises a DNA selected from the group consisting of:

(A) DNA which encodes a polypeptide comprising the amino acid sequence shown in SEQ ID NO: 4, (B) DNA which encodes a polypeptide comprising an amino acid sequence in which one or several amino acids are deleted, substituted, inserted, or added in the amino acid sequence shown in SEQ ID NO: 4, (C) DNA which comprises the base sequence shown in SEQ ID NO: 3, (D) DNA which comprises a base sequence in which one or several bases are deleted, substituted, inserted, or added in the base sequence shown in SEQ ID NO: 3, and (E) DNA which hybridizes under stringent conditions to DNA set forth in any one of (A) to (D);

(3) DNA of the above (1) which comprises a DNA selected from the group consisting of:
  (F) DNA which encodes a polypeptide comprising the amino acid sequence shown in SEQ ID NO: 6,
  (G) DNA which encodes a polypeptide comprising an amino acid sequence in which one or several amino acids are deleted, substituted, inserted, or added in the amino acid sequence shown in SEQ ID NO: 6,
  (H) DNA which comprises the base sequence shown in SEQ ID NO: 5,
  (I) DNA which comprises a base sequence in which one or several bases are deleted, substituted, inserted, or added in the base sequence shown in SEQ ID NO: 5, and
  (J) DNA which hybridizes under stringent conditions to DNA set forth in any one of (F) to (I);

(4) DNA of the above (1) which comprises both of a DNA selected from the group consisting of the following (A) to (E) and a DNA selected from the group consisting of the following (F) to (J):
  (A) DNA which encodes a polypeptide comprising the amino acid sequence shown in SEQ ID NO: 4,
  (B) DNA which encodes a polypeptide comprising an amino acid sequence in which one or several amino acids are deleted, substituted, inserted, or added in the amino acid sequence shown in SEQ ID NO: 4,
  (C) DNA which comprises the base sequence shown in SEQ ID NO: 3,
  (D) DNA which comprises a base sequence in which one or several bases are deleted, substituted, inserted, or added in the base sequence shown in SEQ ID NO: 3,
  (E) DNA which hybridizes under stringent conditions to DNA set forth in any one of (A) to (D),
  (F) DNA which encodes a polypeptide comprising the amino acid sequence shown in SEQ ID NO: 6,
  (G) DNA which encodes a polypeptide comprising an amino acid sequence in which one or several amino acids are deleted, substituted, inserted, or added in the amino acid sequence shown in SEQ ID NO: 6,
  (H) DNA which comprises the base sequence shown in SEQ ID NO: 5,
  (I) DNA which comprises a base sequence in which one or several bases are deleted, substituted, inserted, or added in the base sequence shown in SEQ ID NO: 5, and
  (J) DNA which hybridizes under stringent conditions to DNA set forth in any one of (F) to (I);

(5) DNA of the above (1) which comprises a DNA selected from the group consisting of:
  (K) DNA which encodes a polypeptide comprising the amino acid sequence shown in SEQ ID NO: 2,
  (L) DNA which encodes a polypeptide comprising an amino acid sequence in which one or several amino acids are deleted, substituted, inserted, or added in the amino acid sequence shown in SEQ ID NO: 2,
  (M) DNA which comprises the base sequence shown in SEQ ID NO: 1,
  (N) DNA which comprises a base sequence in which one or several bases are deleted, substituted, inserted, or added in the base sequence shown in SEQ ID NO: 1, and
  (O) DNA which hybridizes under stringent conditions to DNA set forth in any one of (K) to (N);

(6) a single-chain antibody capable of binding to hepatitis B virus core protein, the antibody being encoded by DNA set forth in any one of the above (1) to (5);

(7) a vector containing DNA set forth in any one of the above (1) to (5);

(8) a transformant transformed with a vector of the above (7);

(9) a process for producing a single-chain antibody capable of binding hepatitis B virus core protein, the process being characterized in that a transformant of the above (8) is cultured under conditions which allow expression of the single-chain antibody encoded by DNA set forth in any one of the above (1) to (5);

(10) a therapeutic agent for hepatitis B comprising a single-chain antibody of the above (6) as an active ingredient;

(11) a gene therapy agent against hepatitis B comprising DNA set forth in any one of the above (1) to (5) as an active ingredient;

(12) a gene therapy agent of the above (11) characterized in that it uses an adenoviral vector; and

(13) a gene therapy agent of the above (11) or (12) wherein hepatitis B is acute or chronic hepatitis.

The present invention is described in detail below.

The DNA of the present invention is characterized in that it encodes a single-chain antibody capable of binding to hepatitis B virus core protein. In general, a single-chain antibody is composed of a contiguous peptide in which an appropriate linker sequence encoding a highly flexible peptide sequence is sandwiched between $V_H$ and $V_L$ moieties of an antibody.

Specific examples are the following 1) to 3):

1) a single-chain antibody which comprises $V_H$ moiety consisting of the amino acid sequence shown in SEQ ID NO: 4 or another moiety functionally equivalent to said $V_H$ moiety and which is capable of binding to hepatitis B virus core protein;

2) a single-chain antibody which comprises $V_L$ moiety consisting of the amino acid sequence shown in SEQ ID NO: 6 or another moiety functionally equivalent to said $V_L$ moiety and which is capable of binding to hepatitis B virus core protein; and 3) a single-chain antibody which develops its ability to bind to hepatitis B virus core protein by combining $V_H$ moiety consisting of the amino acid sequence shown in SEQ ID NO: 4 or another moiety functionally equivalent to said $V_H$ moiety with $V_L$ moiety consisting of the amino acid sequence shown in SEQ ID NO: 6 or another moiety functionally equivalent to said $V_L$ moiety.

A DNA encoding a single-chain antibody which meets the requirements of the above 1) may be, for example, DNA which comprises a DNA selected from the group consisting of:

(A) DNA which encodes a polypeptide comprising the amino acid sequence shown in SEQ ID NO: 4, (B) DNA which encodes a polypeptide comprising an amino acid sequence in which one or several amino acids are deleted, substituted, inserted, or added in the amino acid sequence shown in SEQ ID NO: 4, (C) DNA which comprises the base sequence shown in SEQ ID NO: 3, (D) DNA which comprises a base sequence in which one or several bases are deleted, substituted, inserted, or added in the base sequence shown in SEQ ID NO: 3, and (E) DNA which hybridizes under stringent conditions to DNA set forth in any one of (A) to (D); and which encodes a single-chain antibody capable of binding to hepatitis B virus core protein.

Since the base sequence shown in SEQ ID NO: 3 is that of DNA encoding $V_H$ moiety of an antibody against hepatitis B virus core protein, and the amino acid sequence shown in SEQ ID NO: 4 is the amino acid sequence deduced from the base sequence shown in SEQ ID NO: 3, DNAs of the above (A) to (E) are those DNAs that encode $V_H$ moiety of an antibody against hepatitis B virus core protein or another polypeptide functionally equivalent to said $V_H$ moiety.

Likewise, a DNA encoding a single-chain antibody which meets the requirements of the above 2) may be, for example, DNA which comprises a DNA selected from the group consisting of:

(F) DNA which encodes a polypeptide comprising the amino acid sequence shown in SEQ ID NO: 6, (G) DNA which encodes a polypeptide comprising an amino acid sequence in which one or several amino acids are deleted, substituted, inserted, or added in the amino acid sequence shown in SEQ ID NO: 6, (H) DNA which comprises the base sequence shown in SEQ ID NO: 5, (I) DNA which comprises a base sequence in which one or several bases are deleted, substituted, inserted, or added in the base sequence shown in SEQ ID NO: 5, and (J) DNA which hybridizes under stringent conditions to DNA set forth in any one of (F) to (I); and which encodes a single-chain antibody capable of binding to hepatitis B virus core protein.

Since the base sequence shown in SEQ ID NO: 5 is that of DNA encoding $V_L$ moiety of an antibody against hepatitis B virus core protein, and the amino acid sequence shown in SEQ ID NO: 6 is the amino acid sequence deduced from the base sequence shown in SEQ ID NO: 5, DNAs of the above (F) to (J) are those DNAs that encode $V_L$ moiety of an antibody against hepatitis B virus core protein or another polypeptide functionally equivalent to said $V_L$ moiety.

Furthermore, a DNA encoding a single-chain antibody which meets the requirements of the above 3) may be, for example, DNA which comprises both of a DNA selected from the group consisting of the following (A) to (E) and a DNA selected from the group consisting of the following (F) to (J), and which encodes a single-chain antibody capable of binding to hepatitis B virus core protein:

(A) DNA which encodes a polypeptide comprising the amino acid sequence shown in SEQ ID NO: 4, (B) DNA which encodes a polypeptide comprising an amino acid sequence in which one or several amino acids are deleted, substituted, inserted, or added in the amino acid sequence shown in SEQ ID NO: 4, (C) DNA which comprises the base sequence shown in SEQ ID NO: 3, (D) DNA which comprises a base sequence in which one or several bases are deleted, substituted, inserted, or added in the base sequence shown in SEQ ID NO: 3, (E) DNA which hybridizes under stringent conditions to DNA set forth in any one of (A) to (D), (F) DNA which encodes a polypeptide comprising the amino acid sequence shown in SEQ ID NO: 6, (G) DNA which encodes a polypeptide comprising an amino acid sequence in which one or several amino acids are deleted, substituted, inserted, or added in the amino acid sequence shown in SEQ ID NO: 6, (H) DNA which comprises the base sequence shown in SEQ ID NO: 5, (I) DNA which comprises a base sequence in which one or several bases are deleted, substituted, inserted, or added in the base sequence shown in SEQ ID NO: 5, and (J) DNA which hybridizes under stringent conditions to DNA set forth in any one of (F) to (I).

Such DNA contains both of a DNA encoding $V_H$ moiety of an antibody against hepatitis B virus core protein or another polypeptide functionally equivalent to said $V_H$ moiety and a DNA encoding $V_L$ moiety of said antibody or another polypeptide functionally equivalent to said $V_L$ moiety. Such DNAs which meet the requirements of 3) are more preferable because they encode antibodies that specifically bind to only hepatitis B virus core protein.

Further examples of DNA which meets the requirements of 3) may be those DNAs which have a sequence selected from the group consisting of:

(K) DNA which encodes a polypeptide comprising the amino acid sequence shown in SEQ ID NO: 2, (L) DNA which encodes a polypeptide comprising an amino acid sequence in which one or several amino acids are deleted, substituted, inserted, or added in the amino acid sequence shown in SEQ ID NO: 2, (M) DNA which comprises the base sequence shown in SEQ ID NO: 1, (N) DNA which comprises a base sequence in which one or several bases are deleted, substituted, inserted, or added in the base sequence shown in SEQ ID NO: 1, and (O) DNA which hybridizes under stringent conditions to DNA set forth in any one of (K) to (N), and which encode a single-chain antibody that binds to hepatitis B virus core protein.

In this connection, the base sequence shown in SEQ ID NO: 1 is the base sequence of DNA encoding PRE-HV, $V_H$ moiety of an antibody against hepatitis B virus core protein, linker, $V_L$ moiety of said antibody, and TAIL, and the amino acid sequence shown in SEQ ID NO: 2 is the amino acid sequence deduced from the base sequence shown in SEQ ID NO: 1.

An example of the above DNA that hybridizes under stringent conditions is DNA hybridizing under the conditions in which hybridization is conducted overnight at 42° C. using, as a hybridization buffer, a solution having the composition of 0.1% SDS, 50% formamide, 5×SSC, 1×Denhardt's reagent, and 250 μg/mL salmon sperm DNA, subsequently washed with 2×SSC for 1 hour at room temperature, with 2×SSC, 0.1% SDS for 30 minutes at room temperature, and then with 0.1×SSC, 0.1% SDS for 30 minutes at 50–65° C.

Although the method for introducing deletion, substitution, insertion, or addition of bases or amino acids as described above is not specifically restricted, it can be achieved by introducing a mutation into the objective base sequence using a method which uses restriction enzyme, nuclease, or the like, or using site-directed mutagenesis (W. ITO et al., Gene, 102, 67–70 (1991), incorporating the product into a vector for expression, and transforming host cells with that vector. Furthermore, although the term "several" is not specifically restricted in connection with the above mutation of base or amino acid, it refers to such a number that permits the deletion, substitution, insertion, or addition by well-known methods such as site-specific mutagenesis described above.

Likewise, the amino acid sequences of the peptides corresponding to PRE-HV, linker, and TAIL in the single-chain antibody, and the base sequences of DNAs encoding said peptides are not specifically restricted, and they may have the amino acid sequences of peptides at corresponding sites in known single-chain antibodies and the base sequences of DNAs encoding said peptides. For example, when a single-chain antibody is prepared using Recombinant Phage Antibody System manufactured by Pharmacia, the amino acid sequences of the peptides corresponding to PRE-HV, linker, and TAIL are those sequence shown in SEQ ID NOs: 8, 10, and 12, respectively, and the base sequences of DNAs encoding said peptides are those sequences shown in SEQ ID NOs 7, 9, and 11, respectively.

In the present invention, DNAs of the present invention can easily be obtained by using a kit for preparation of single-chain antibody such as Recombinant Phage Antibody System manufactured by Pharmacia. Since DNA of the present invention prepared using such a kit is obtained in the form that is incorporated in a vector, expression of the single-chain antibody may be achieved more easily.

A method for preparing DNA of single-chain antibody of the present invention is described in detail below. An anti-hepatitis B virus core protein antibody can be produced in an animal by immunizing the animal with a mixture of hepatitis B virus core protein as the antigen, and an adjuvant.

The animal to be immunized is not specifically restricted, and may be, for example, rabbit, guinea pig, goat, donkey, fowl, rat, and mouse (Balb/c mouse, SWISS 3T3 mouse, C3H mouse, C57BL/6 mouse, and the like).

The hepatitis B virus core protein used as the antigen may be obtained, for example, by gene recombinant techniques (*J. Electron Microsc.*, (Tokyo), 43(6), 386–393 (1994)).

The adjuvant is not specifically restricted, and may be a known adjuvant commonly used, for example, Freund's complete or incomplete adjuvant.

According to the usual method, cDNA may be obtained by purifying poly(A)-RNA from the spleen of the immunized animal, preparing mRNA, and reverse-transcribing such mRNA.

Although the method for obtaining DNAs encoding $V_H$ and $V_L$ moieties of an antibody against hepatitis B virus core protein from such cDNA is not specifically restricted, they may be obtained, for example, from cDNA library by hybridization using nucleic acid probes specific for $V_H$ and $V_L$ moieties, respectively, or by specifically amplifying $V_H$ and $V_L$ moieties using PCR method.

When PCR method is used, for example, cDNAs encoding $V_H$ and $V_L$ moieties, respectively, can be obtained by conducting PCR with primer pairs specific for $V_H$ and $V_L$ moieties, respectively, under conditions that allows specific amplification using the above cDNA as template. As such a specific primer pair, those primers included in the above-mentioned Recombinant Phage Antibody System may be used.

The cDNAs for $V_H$ or $V_L$ moieties obtained may be each converted into double-stranded cDNA, and they may be ligated to a vector such as a phagemid vector after blunting the termini or after introducing restriction enzyme sites using a method such as PCR or site-specific mutagenesis and treating with restriction enzymes.

For example, the respective cDNAs for $V_H$ and $V_L$ moieties obtained as described above are ligated in a linear from to a DNA encoding a liker region, and restriction enzyme sites are further introduced into the contiguous linear DNA having the structure of $V_H$-linker-$V_L$ by conducting PCR using a primer pair corresponding to the contiguous linear DNA having the structure of $V_H$-linker-$V_L$ each of which primers has a restriction enzyme recognition sequence at its 5' end in order to facilitate the ligation to a vector.

In this process, it is preferable to use a vector which has been constructed so that the DNA encoding PRE-HV and the DNA encoding TAIL will be connected to the ends of DNA encoding $V_H$ moiety-linker-DNA encoding $V_L$ moiety. An example of such vector is the phagemid vector pCANTAB5E included in Recombinant Phage Antibody System manufactured by Pharmacia.

The DNA of the present invention obtained by using such a kit is in the form that is incorporated in a vector. Therefore, a recombinant phage displaying a single-chain antibody can be obtained by transforming *E. coli* with said vector and then infecting the obtained *E. coli* clone with a helper phage.

A single-chain antibody of the present invention is a protein encoded by DNA of the present invention which fulfills one of the above-described requirements 1), 2) and 3).

One can determine whether or not the single-chain antibody described in the present specification is capable of binding to hepatitis B virus core protein, using ELISA by measurement of fluorescence intensity. In this procedure, a single-chain antibody of which fluorescence intensity is clearly higher than that of a negative control using a single-chain antibody which does not bind to hepatitis B virus core protein, and is reproducibly detectable is considered as a single-chain antibody capable of binding to hepatitis B virus core protein.

Vectors of the present invention are those vectors that contain the above-described DNA of the present invention. A vector used in constructing vectors of the present invention is not specifically restricted so long as it is a vector that allows expression of the single-chain antibody encoded by said DNA. A specific example is a phagemid vector pCANTAB5E (Pharmacia) when the host is *E. coli*, or pZeoSV2 (Invitrogen) when the host is a mammalian cell. The method for inserting the DNA of the present invention into the vector is not specifically restricted, and may be a known method, for example, using T4 DNA ligase.

Transformants of the present invention can be obtained by introducing a vector of the present invention into desired host cells.

Host cells are not specifically restricted, and include, for example, human cells such as hepatoma-derived HepG2, Chang liver cells, and kidney-derived adenovirus EIA and EIB transformed cells (293), animal cells such as COS-1, COS-7, CHO, and NIH 3T3, insect cells such as armyworm-derived Sf9 cells, yeasts, and *E. coli* such as *E. coli* strain K12 derivatives. For the purpose of expressing a human-derived single-chain antibody against HBV, it is more preferred to use human-derived cultured cells.

In order to introduce a vector containing DNA of the present invention into host cells, such a method as the calcium phosphate method, electroporation, lipofection, or recombinant viral infection may be used.

A process of the present invention for producing a single-chain antibody capable of binding to hepatitis B virus core protein is characterized in that a transformant of the present invention is cultured under conditions that allow expression of the single-chain antibody encoded by DNA of the present invention. As the conditions that allow expression of the gene product encoding a single-chain antibody that has been incorporated into the vector containing the DNA of the present invention, it is required that transcription from a promoter in the vector located upstream to the DNA of the present invention works effectively, and that an open reading frame for correct amino acids must can be assigned in the translation.

Expression of single-chain antibody of the present invention can be confirmed using a method as described above by measuring the ability of the obtained single-chain antibody to bind to hepatitis B virus core protein.

Purification of anti-core protein single-chain antibody from the recombinant may be achieved by a conventional known method. For example, cultured cells may be broken and the desired single-chain antibody expressed may be obtained from the supernatant, for example, by affinity column chromatography. Specifically, in the present invention, the antibody can easily be purified by affinity column chromatography against E-tag at the C-terminus of the expressed anti-core protein single-chain antibody. The anti-core protein single-chain antibody obtained as described above has an ability to suppress DNA synthesis of the virus by binding to hepatitis B virus core protein, and can further achieve the effect of suppressing propagation of the virus.

A therapeutic agent for hepatitis B of the present invention may be used as a therapeutic agent that comprises as an active ingredient an anti-core protein single-chain antibody of the present invention as such, or may be used as a gene therapy agent by which DNA encoding an anti-core protein single-chain antibody is administered into a patient as an active ingredient of the pharmaceutical agent and the gene is expressed in the body of the patient.

A therapeutic agent that comprises as an active ingredient an anti-core protein single-chain antibody as such may be administered with an adjuvant or administered in a particulate dosage form. More particularly, the dosage forms such as liposome formulations, particulate formulations in which the active ingredient is attached to beads having a diameter of several $\mu$m, and formulations in which lipids are attached to the ingredient may be used. Administration may be achieved, for example, by means of sustained-release minipellet formulations. Furthermore, peptides that enhance the efficiency with which the antibody is transferred across the cell membrane may also be added. In particular, hydrophobic regions are connected to the N- and C-termini of the single-chain antibody. It is also possible to enhance the permeability of the cell membrane by attaching a particular carbohydrate chain. Although the amount administered may be adjusted as appropriate depending on the amount of hepatitis B virus carried by the patient, the age, weight of the patient, and the like, it is typically 0.001 mg/kg/dose to 1000 mg/kg/dose administered for consecutive days at the beginning and then administered once every several days or several months. Regarding the mode of administration, the agent can be administered orally, intraarterially, intravenously, or intramuscularly depending on the dosage form.

When used as a gene therapy agent, the present agent can highly express an anti-core protein single-chain antibody intracellularly, thereby suppress replication of the viral DNA in cells infected with hepatitis B virus, and further suppress propagation of the virus.

In the case that a gene therapy agent comprising as an active ingredient DNA encoding an anti-core protein single-chain antibody is introduced into infected cells, the modes of administration are broadly divided into two kinds of embodiments, one using non-viral vector and the other using viral vector. In particular, representative examples of the former embodiments are those methods in which a DNA molecule of the present invention is directly introduced into cells (such as a method in which an expression plasmid is directly administered intramuscularly), those methods in which the DNA molecule is introduced using liposome (such as the liposome method or the lipofectin method), those methods in which the DNA molecule is transferred into cells together with a carrier using a particle gun, microinjection, the calcium phosphate method, and electroporation.

Representative examples of the latter embodiments are those methods that use viral vectors such as recombinant adenoviruses or retroviruses, and in particular, include those methods in which DNA encoding an anti-core protein single-chain antibody is incorporated into a DNA or RNA virus such as nontoxic retrovirus, adenovirus, adeno-associated virus, herpesvirus, vaccinia virus, poxvirus, poliovirus, Sindbis virus, or Sendai virus, and introduced into cells.

Among these viruses, adenovirus is known to have a very high transferability into the liver tissue, and also to exhibit an infection efficiency much higher than other viral vectors. It is therefore preferred to use an adenoviral vector system.

By using one of these methods, an anti-core protein single-chain antibody gene can be introduced into hepatitis B virus-infected cells. Furthermore, in the case of gene therapies using non-viral vectors, it is desired to guide the gene to the vicinity of infected cells, for example, by local administration, whereas in the case of gene therapies using viral vectors, it is not necessarily required to locally administer the agent, and intravenous administration is also possible.

As methods by which a gene therapy agent of the present invention is allowed to act as a pharmaceutical in practice, there are an in vivo method in which DNA is directly introduced into the body, and an ex vivo method in which certain cells are removed from a human, DNA is introduced into said cells ex vivo, and the cells are returned into the body (*Nikkei Science*, April, 1994, pp. 20–45 and September, 1997, pp. 27–62; *Gekkan-Yakuji*, 36 (1), 23–48 (1994); and *Jikkenn-Igaku*, 12 (15), 1994). In the present invention, an in vivo method is more preferred. Although the content of DNA in the formulation may be adjusted as appropriate depending on the disease to be treated, the age, weight of the patient, and the like, it is typically 0.0001–100 mg, and preferably 0.001–10 mg, administered once every several days or several months.

The therapeutic agents for hepatitis B comprising as an active ingredient an anti-core protein single-chain antibody, and the gene therapy agents against hepatitis B comprising, as an active ingredient, a DNA encoding an anti-core protein single-chain antibody are those agents against hepatitis B caused by hepatitis B virus, and said hepatitis B may be acute or chronic hepatitis.

BRIEF DESCRIPTION OF THE DRAWINGS

FIG. 1 is a graph indicating absorbance in ELISA using clones 1C9 and γ9.

FIG. 2 is a photograph of electrophoretic gel indicating the result of Western blot analysis. Left lane: molecular weight marker (30 KDa); right lane: the periplasm of HB2151 infected with 1C9 antibody-producing phage (sFv).

FIG. 3 is a photograph of electrophoretic gel indicating the result of Northern blot analysis on mRNA for single-chain antibody. Lanes 1–3: RNAs derived from clones (N4, N7, and N8) obtained by introducing pZeoSVγ9; lanes 4–6: RNAs (P3, P8, and P9) derived from clones obtained by introducing pZeoSV1C9.

FIG. 4 is a photograph of electrophoretic gel indicating the result of the same analysis as in FIG. 3 conducted on other clones. Lanes 1–4: RNAs ("sFv" in the figure) derived from clones (P9, P12-1, P10, and P20) obtained by introducing pZeoSV1C9; lanes 5 and 6: RNAs ("sFv" in the figure) derived from clones (N4 and N8) obtained by introducing pZeoSVγ9.

FIG. 5 is a photograph of electrophoretic gel indicating the result of Northern blot analysis on mRNA of HBV. Lanes 1–3: RNAs derived from clones (N4, N7, and N8) obtained by introducing pZeoSVγ9: RNAs derived from clones (P3, P8, and P9) obtained by introducing pZeoSV1C9.

Figure 1:
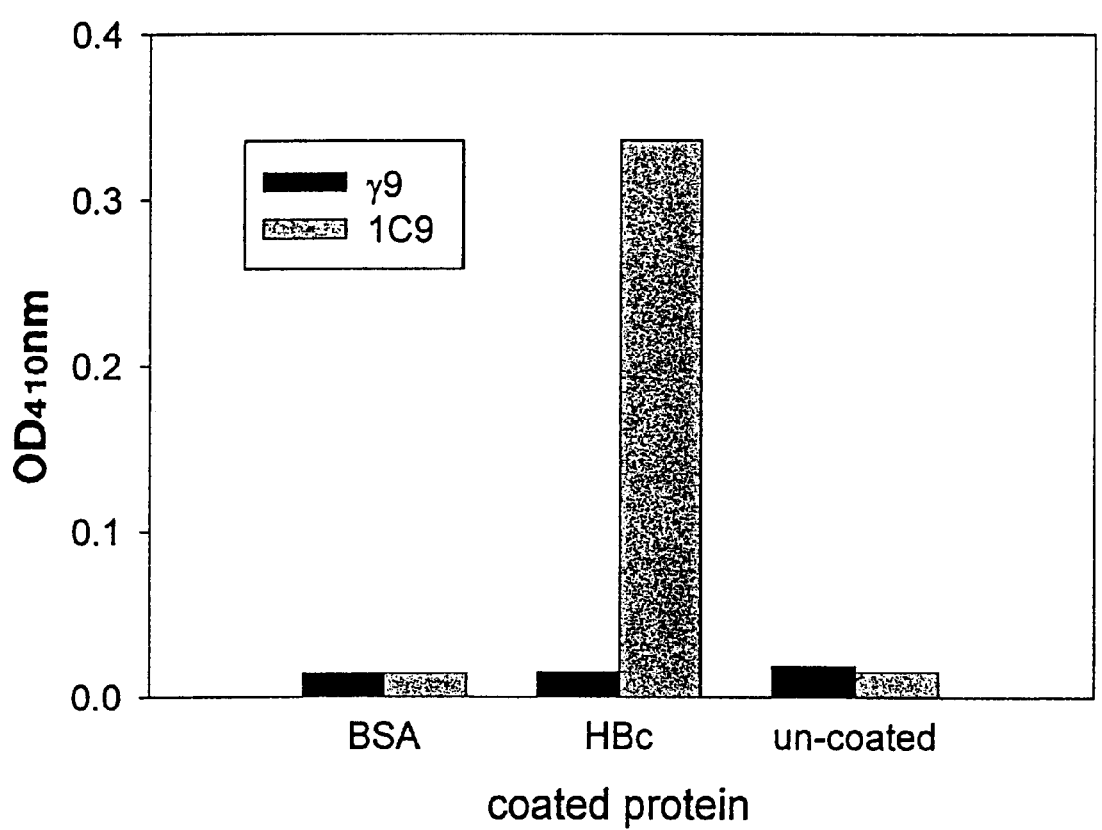

Hepatitis B viral DNA in chromosomal DNA of the transformants are found at the position of band "I", and replicative intermediate DNAs of hepatitis B virus are found at the positions of bands "S" (single-stranded DNA) and "$D_1$" (linear double-stranded DNA). Lane 1 indicates molecular markers (1 kb ladder); lanes 2–7 indicate DNAs derived from clones obtained by introducing pZeoSVγ9 (lanes 2 and 3: N4 DNA; lanes 4 and 5: N7 DNA; and lanes 6 and 7: N8 DNA); and lanes 8–14 indicate DNAs derived from clones obtained by introducing pZeoSV1C9 (lanes 8 and 9: P3 DNA; lanes 10 and 11: P8 DNA; lanes 12 and 13: P9 DNA).

Figure 7:
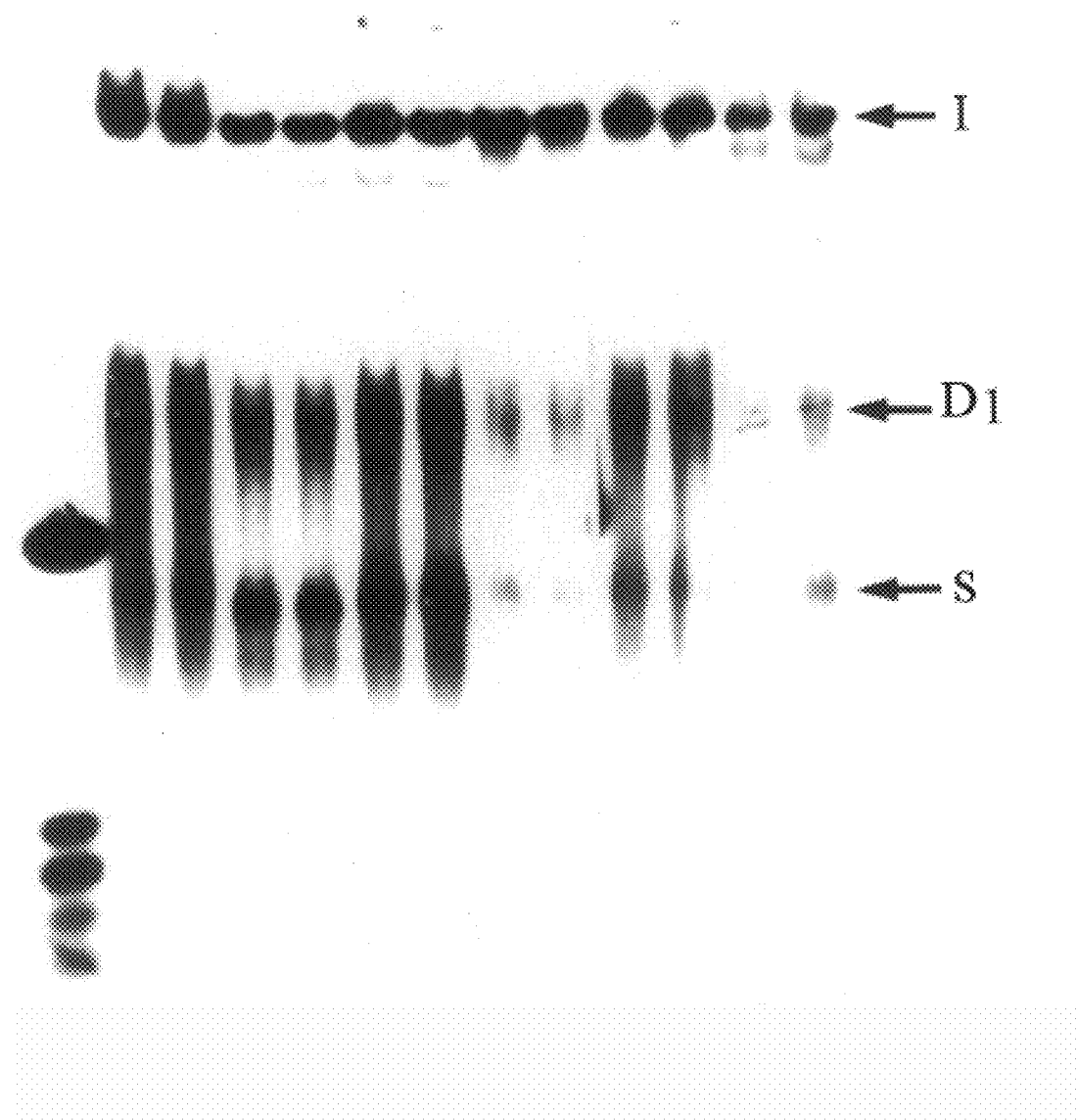
FIG. 7 is a photograph of electrophoretic gel indicating the result of Southern blot analysis of hepatitis B viral DNA derived from transformants.
Figure 8:
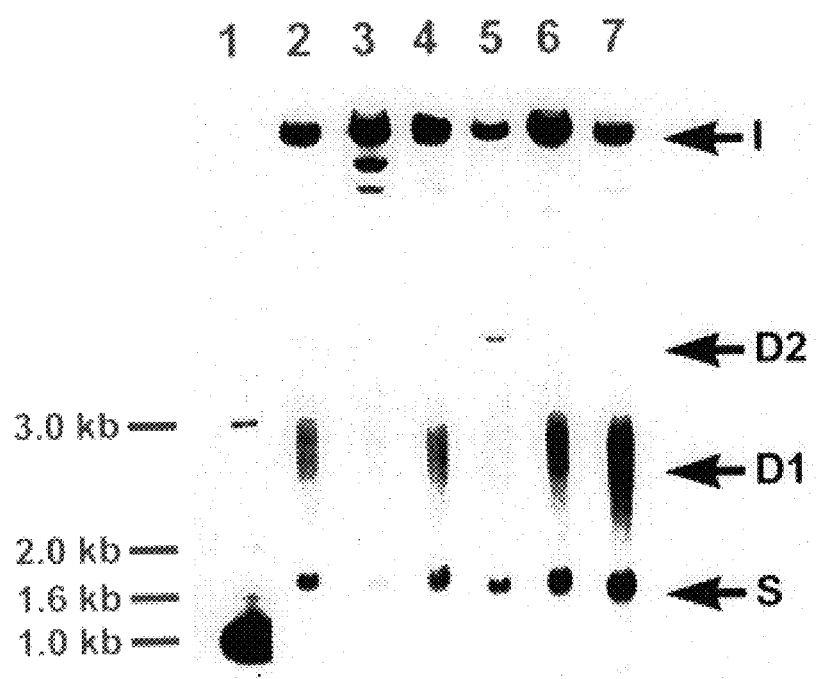

FIG. 8 is a photograph of electrophoretic gel indicating the result of the same analysis as in FIG. 7 conducted on other clones. In the figure, I, D1, and S respectively indicate the same means as in FIG. 7. D2 indicates the circular double-stranded DNA. Lane 1: molecular markers; lanes 2–5: DNAs derived from clones (P9, P12-2, p10, and p20) obtained by introducing pZeoSV1C9; lanes 6 and 7: DNAs derived from clones (N4 and N8) obtained by introducing pZeoSVγ9.

Figure 9:
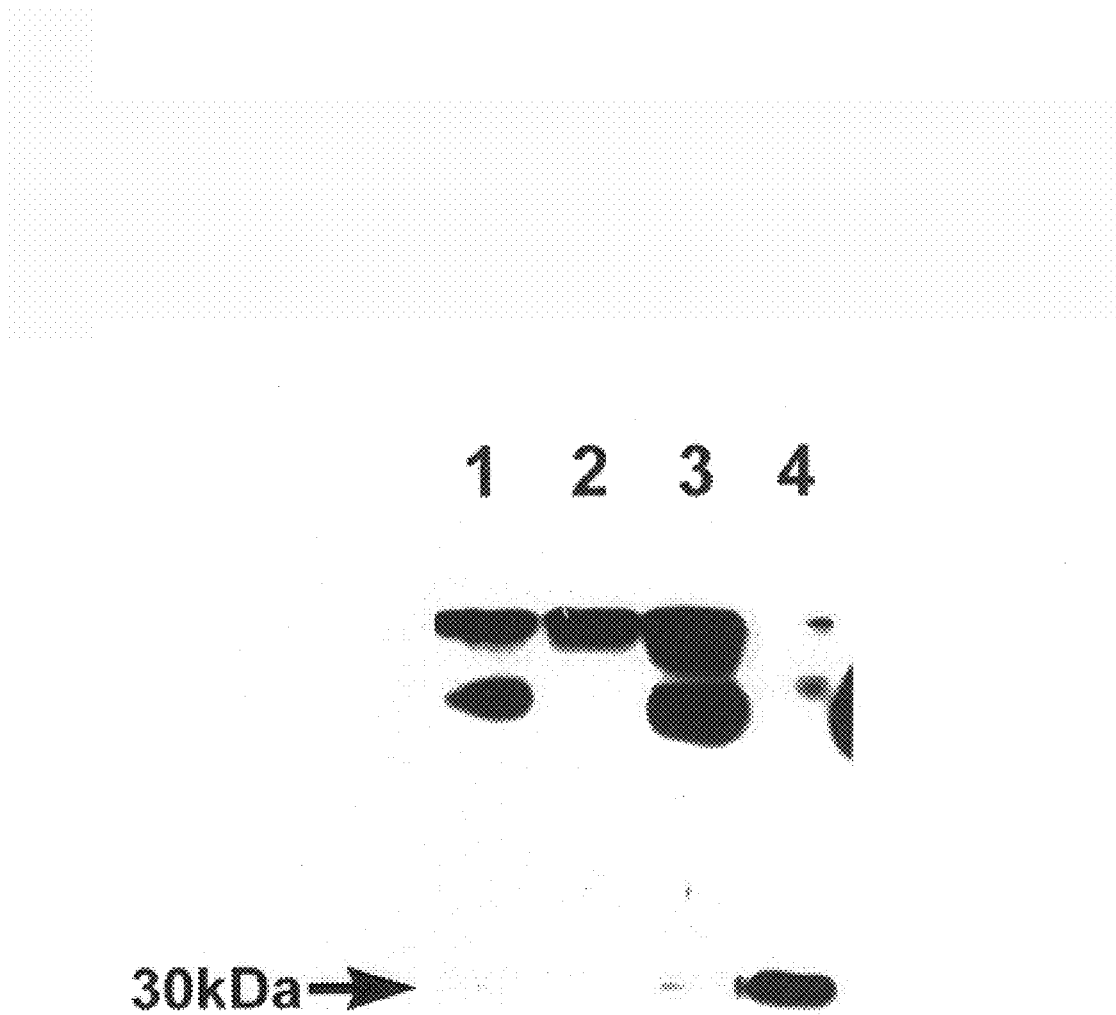

FIG. 9 is a photograph of electrophoretic gel indicating the result of Western blot analysis of immunoprecipitated proteins. Proteins derived from a clone (N8) obtained by introducing pZeoSVγ9 after immunoprecipitation with anti-sera (lane 1) or an anti-HBV core protein antibody (lane 2) are shown. Proteins derived from a clone (P12-2) obtained by introducing pZeoSV1C9 after immunoprecipitation with antisera (lane 3) or an anti-HBV core protein antibody (lane 4) are also shown.

Figure 10:
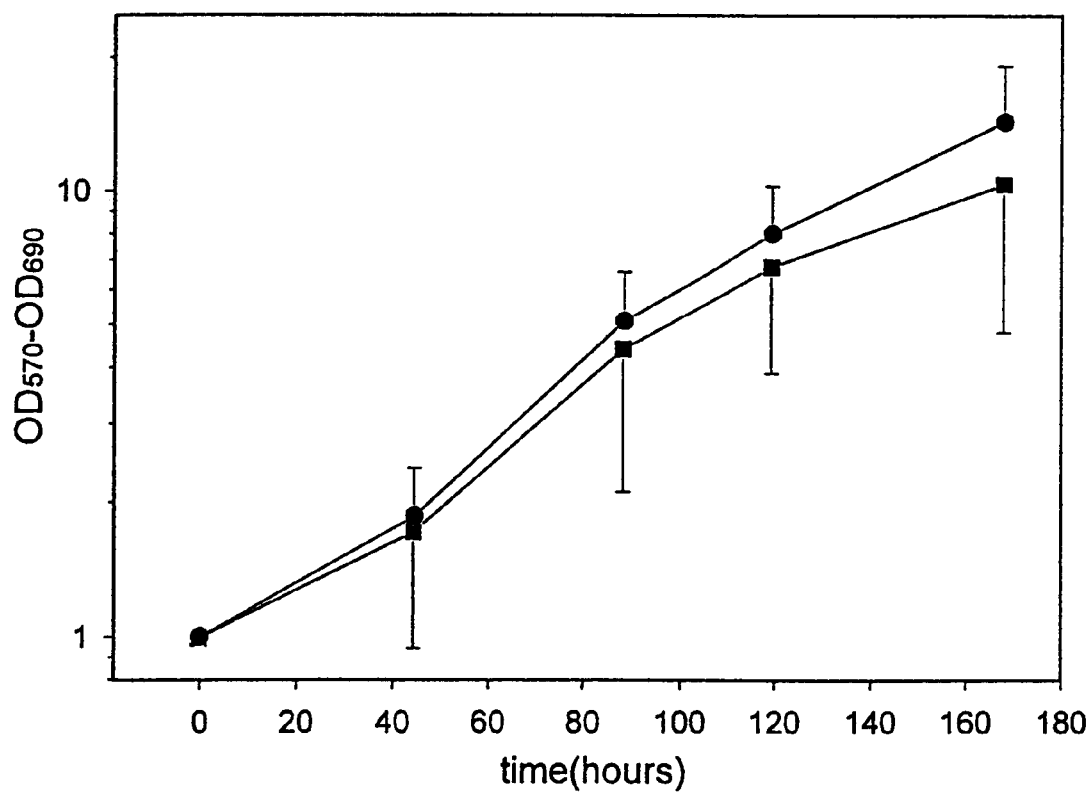

FIG. 10 is a graph indicating cell growth of pZeoSV1C9-introduced HB 611 cells and pZeoSVγ9-introduced HB 611 cells. The character "■" corresponds to pZeoSV1C9-introduced HB 611 cells, and "●" corresponds to pZeoSVγ9-introduced HB 611 cells.

Figure 11A:
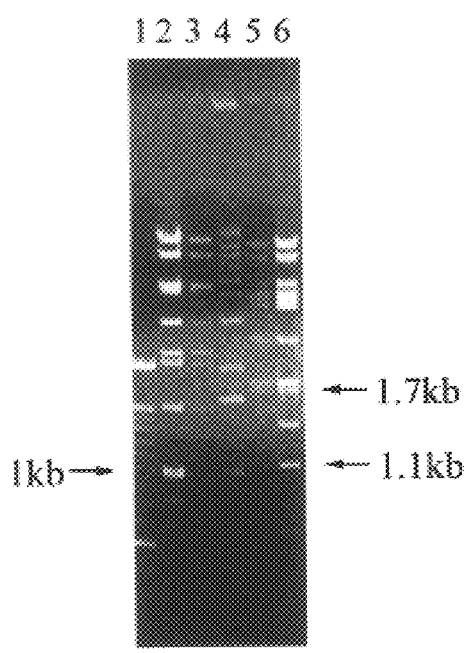
Figure 11B:
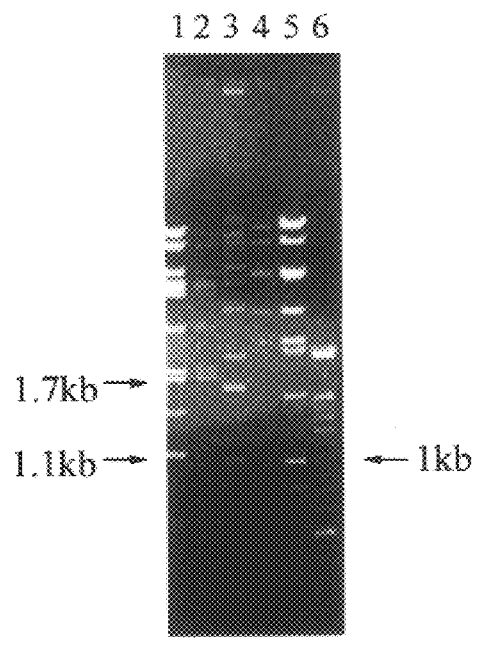

FIG. 11 is photographs of electrophoretic gels indicating the result of cleavage by restriction enzymes of cosmid clone DNAs into which a single-chain antibody gene has been inserted. The left photograph (A) shows the result of cleavage of a cosmid vector containing the inserted 1C9 gene, and the right photograph (B) shows the result of cleavage of a cosmid vector containing the inserted γ9 gene. (A) Lanes 2 and 3: Hind III, Xba I digested; lanes 5 and 6: Nhe I, Spe I digested; lanes 1 and 4: size markers; (B) lanes 1 and 2: Nhe I, Spe I digested; lanes 4 and 5: Hind III, Xba I digested; lanes 3 and 6: size markers.

Figure 12A:
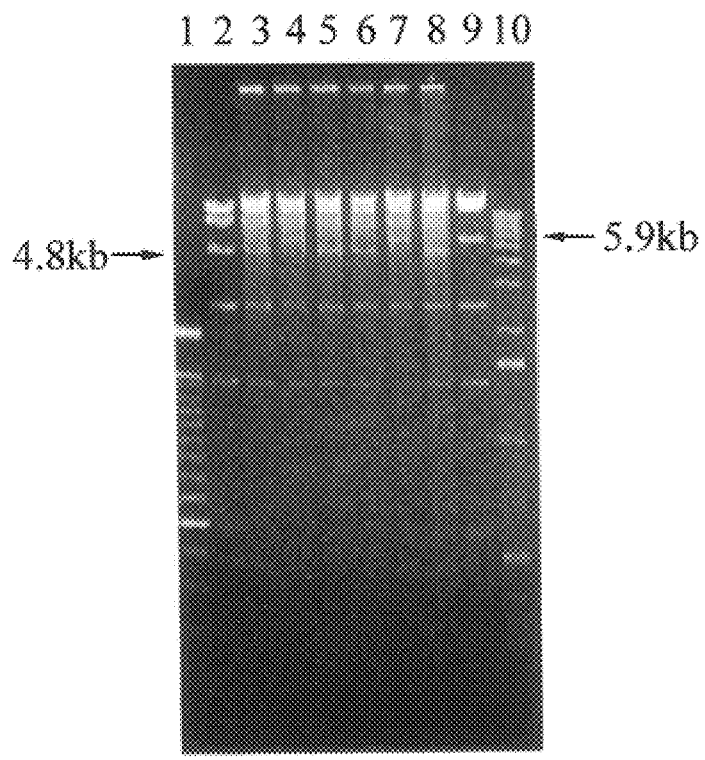
Figure 12B:
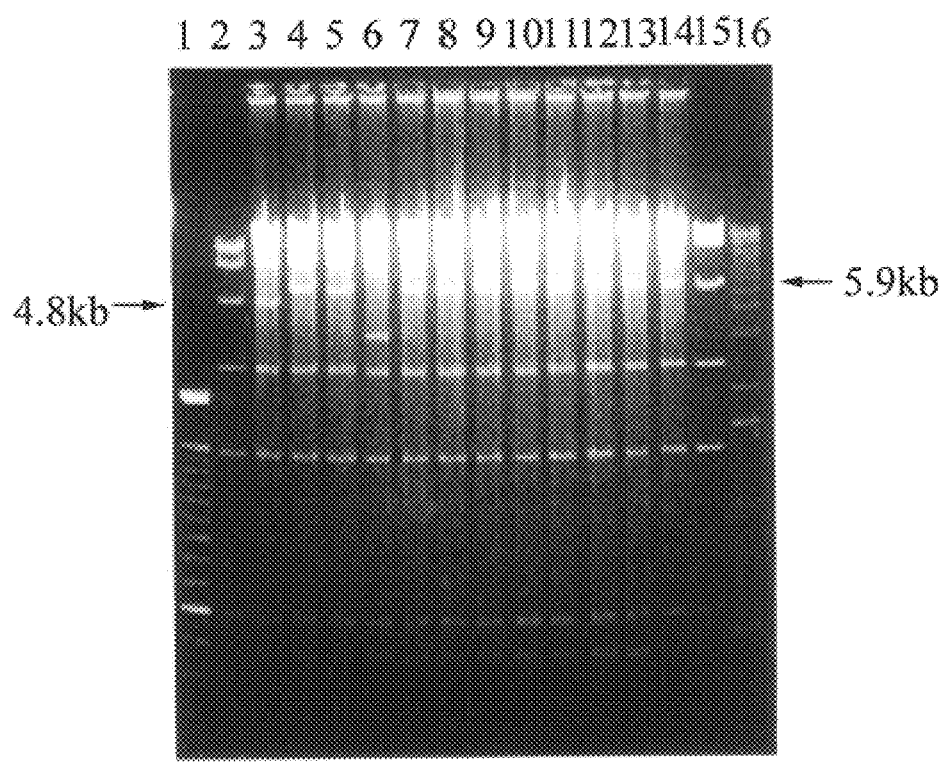

FIG. 12 is photographs of electrophoretic gels indicating the result of cleavage by restriction enzyme Xho I of various adenoviral vector DNAs expressing a single-chain antibody. Photograph (A) corresponds to clones of an adenoviral vector containing the 1C9 gene, and photograph (B) corresponds to clones of an adenoviral vector containing the γ9 gene. (A) Lanes 1 and 10: size markers; lane 2: Ax1CAwt; lane 9: a 1C9 gene-inserted cosmid; lanes 3–8: various adenoviral clones; (B) lanes 1 and 16: size markers; lane 2: Ax1Cawt; lane 15: a γ9 gene-inserted cosmid; lanes 3–14: various adenoviral clones.

BEST MODE FOR CARRYING OUT THE INVENTION

The present invention is described in more detail with reference to the following examples, but the present invention is not limited to these examples in any way.

EXAMPLE 1

Preparation of Cell Culture and Immunized Animals

Human hepatoblastoma-derived cell line persistently producing hepatitis virus B (HB611; provided by Prof. Kenichi Matsubara of Osaka University, Institute for Molecular and Cellular Biology/Nara Institute of Science and Technology; or similar cells may be prepared according to *Proc. Natl. Acad. Sci. USA*, 84(2), 444–448 (1987)) was cultured in plastic tissue culture plates (Corning Glass Ware, Corning Inc.) using Dulbecco's modified Eagle's medium (Gibco BRL) supplemented with 10% fetal bovine serum. Cultivation of HB611 were conducted under the conditions at 37° C. and 5% $CO_2$. Concentrations of Zeocin (Invitrogen) and G418 used for selecting resistant strains were 125 μg/mL and 200 μg/mL, respectively.

Immunization of mice was conducted as follows. A mixture of hepatitis B virus core protein antigen (50 μg/250 μL PBS, Chemo-Sero-Therapeutic Research Institute) and 250 μL of Freund's complete adjuvant (Difco) was subcutaneously administered into three Balb/c mice each weighing about 20 g. Boosters were administered twice at intervals of 10 days using Freund's incomplete adjuvant (Difco), and the mouse producing the highest amount of anti-core protein antibody was then received a final booster by intravenous administration of hepatitis B virus core protein antigen (20 μg). After three days, the mouse spleen was sacrificed, total RNA was extracted therefrom using Trisol (Gibco BRL), and poly (A)-RNA was purified using Fast-track (Invitrogen).

EXAMPLE 2

Cloning and Screening of Anti-hepatitis B Virus Core Protein Single-chain Antibody Preparation of cDNA for a single-chain antibody against hepatitis B virus core protein antigen was conducted using Recombinant Phage Antibody System (Pharmacia)

The experimental procedures are outlined below. After reverse transcription was conducted with 25 μg of mRNA obtained above, cDNAs for $V_H$ and $V_L$ moieties were amplified by PCR method using primer pairs specific for the sequences of $V_H$ and $V_L$ moieties, respectively. The cDNAs for $V_H$ and $V_L$ moieties were ligated together in a linear form using a DNA linker sequence, and the product was then amplified by PCR method using a pair of primers having restriction enzyme recognition sequences at their termini. The DNA thus obtained was treated with restriction enzymes, and then inserted into Sfi I and Not I cleavage sites of a phagemid (pCANTAB5E). The phagemid pCANTAB5E contains DNAs corresponding to PRE-HV and TAIL of a single-chain antibody.

To obtain recombinant single-stranded phages displaying single-chain antibodies, *Escherichia coli* TG1 cells was transformed with a phagemid vector containing the PCR-amplified fragment, and the *E. coli* clones were infected with a helper phage M13K07 to prepare recombinant phages displaying single-chain antibodies. In order to select from these phages those having binding ability to hepatitis B virus core protein antigen, the recombinant phage solution was added to a tissue culture flask onto which the core protein antigen was immobilized, and the recombinant phages bound to the core protein antigen were used to infect again TG1 cells.

After the above screening procedures were repeated twice in all, the phage single-chain antibodies were produced from 95 *E. coli* clones obtained, and the ability of the phage single-chain antibody to bind the antigen was examined for each of the isolated clones by an indirect ELISA method using ELISA plates onto which the core protein antigen was adsorbed. As a result, one clone (1C9) out of 95 clones exhibited an absorbance comparable to a positive control, and a phage clone which produced a phage single-chain antibody having a strong binding ability to the core protein antigen was thus obtained. The results are shown in FIG. 1.

The primer pairs specific for each sequence of $V_H$ and $V_L$ moiety, the DNA linker sequence, the pair of primers having restriction enzyme recognition sequences at their termini, the phagemid pCANTAB5E, and the helper phage M13K07 are included in Recombinant Phage Antibody System (Pharmacia).

EXAMPLE 3

Binding Specificity of the Selected Clone 1C9

In order to confirm that the binding ability of clone 1C9 is not due to nonspecific adsorption of a phage vector-derived protein onto the plates, the following examination using ELISA was conducted. Phage antibodies from the positive clone 1C9 and a negative control clone γ9 which produces no phage single-chain antibodies binding to the core protein antigen were examined in wells onto which the core protein antigen (HBc) or bovine serum albumin (BSA) was adsorbed, or in wells which were just blocked with 2% dried skim milk (un-coated). As a result, 1C9 exhibited its binding ability only in the wells containing the core protein antigen adsorbed thereon, and γ9 did not show the binding ability to any of the wells. The result is shown in FIG. 1.

EXAMPLE 4

Determination of the Base Sequence of the Single-chain Antibody Region in Clone 1C9

The DNA fragment encoding the single-chain antibody inserted into the phagemid vector pCANTAB5E derived from the positive clone 1C9 was amplified using Pfu polymerase with primers having Nhe I and Xho I recognition sequences added to their respective termini. The base sequences of primers used are shown in SEQ ID NOs: 13 and 14.

The amplified fragment was temporarily inserted into a cloning vector pBluescript SK(+) (Stratagene) to determine the DNA base sequence.

The base sequence obtained and the deduced amino acid sequence are shown in SEQ ID NOs: 1 and 2, respectively. The base sequences of DNAs encoding $V_H$ and $V_L$ of the anti-core protein antibody are shown in SEQ ID NOs: 3 and 5, respectively, and the deduced amino acid sequences of $V_H$ and $V_L$ are shown in SEQ ID NOs: 4 and 6, respectively.

The amino acid sequences of the moieties corresponding to PRE-HV, linker, and TAIL are shown in SEQ ID NOs: 8, 10, and 12, respectively, and the base sequence of DNAs encoding said peptides are shown in SEQ ID NOs: 7, 9, and 11, respectively. *E. coli* DH5α (pZeoSV1C9) carrying a plasmid pZeoSV1C9 in which the DNA fragment encoding the above single-chain antibody has been incorporated in an expression vector pZeoSV2 after determination of the base sequence has been deposited at the National Institute of Bioscience and Human-Technology, Agency of Industrial Science and Technology (1-1-3, Higashi, Tsukuba, Ibaraki, 305 Japan) (indication of microorganism: *E. coli* DH5α (pZeoSV1C9); date of receipt: Aug. 1, 1997; deposit number: FERM P-216361) (date of transfer to international deposit: Aug. 20, 1998; deposit number: FERM BP-6467).

EXAMPLE 5

Figure 2:
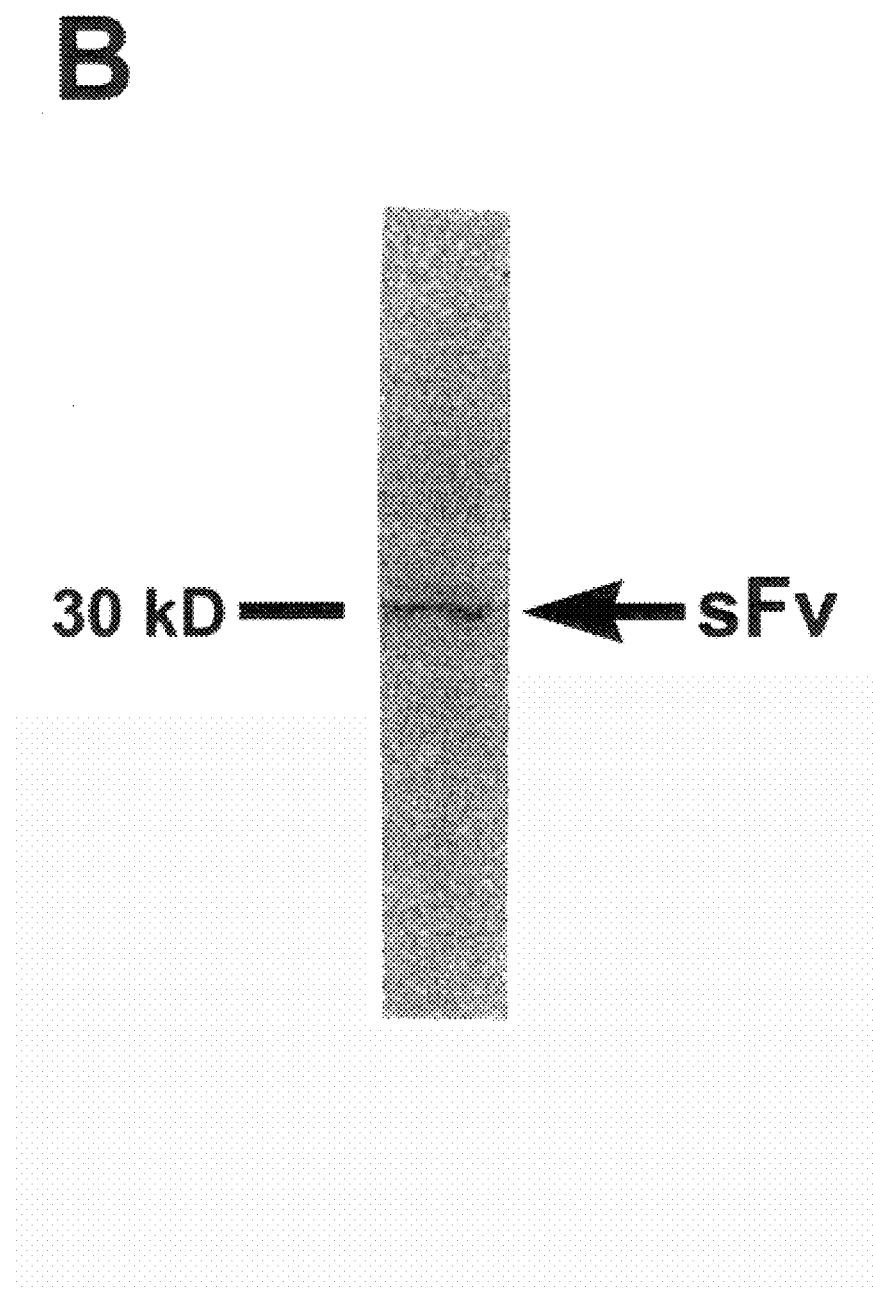

Western Blot Analysis of Soluble Single-chain Antibody Expressed in HB2151 using Anti-E-tag Antibody The recombinant phage derived from 1C9 obtained above was again used to infect *E. coli* HB2151 to produce the soluble single-chain antibody. The clones obtained were treated with 1 mM EDTA to elute a periplasmic solution, and 20 μL of the periplasmic solution was subjected to SDS-PAGE, followed by Western blot analysis using an antibody against E-tag attached to the C terminus of the single-chain antibody. As a result, a single band of about 30 kDa (arrow head) was detected, as shown in FIG. 2 (the right lane).

EXAMPLE 6

Study by Northern Blot Analysis on Expression of RNA Encoding the Single-chain Antibody in the Clone Into Which the Single-chain Antibody Gene has Been Introduced The gene regions which express the single-chain antibodies derived from the positive clone 1C9 and a negative control clone γ9 were inserted into the EcoR I cleavage site of a mammalian cell expression plasmid vector pZeoSV2 (Invitrogen). The obtained recombinant expression vectors pZeoSV1C9 and pZeoSVγ9 were introduced into a human hepatoblastoma-derived cell line producing hepatitis B virus (HB611) by the calcium phosphate method, and for-each vector, three distinct clones exhibiting resistance against Zeocin (pZeoSV1C9-introduced clones: P3, P8, and P9; pZeoSVγ9-introduced clones: N4, N7, N8) were obtained. RNA was prepared from each clone, and Northern blot analysis was conducted using a cDNA fragment sequence of each single-chain antibody as a probe to study the amount of RNA for the single-chain antibody. The Northern analysis was conducted using a filter manufactured by Dupont NEN (Gene screen plus)). Hybridization conditions were in accordance with the protocol provided by Dupont NEN. The results are shown in FIG. 3.

Figure 3:
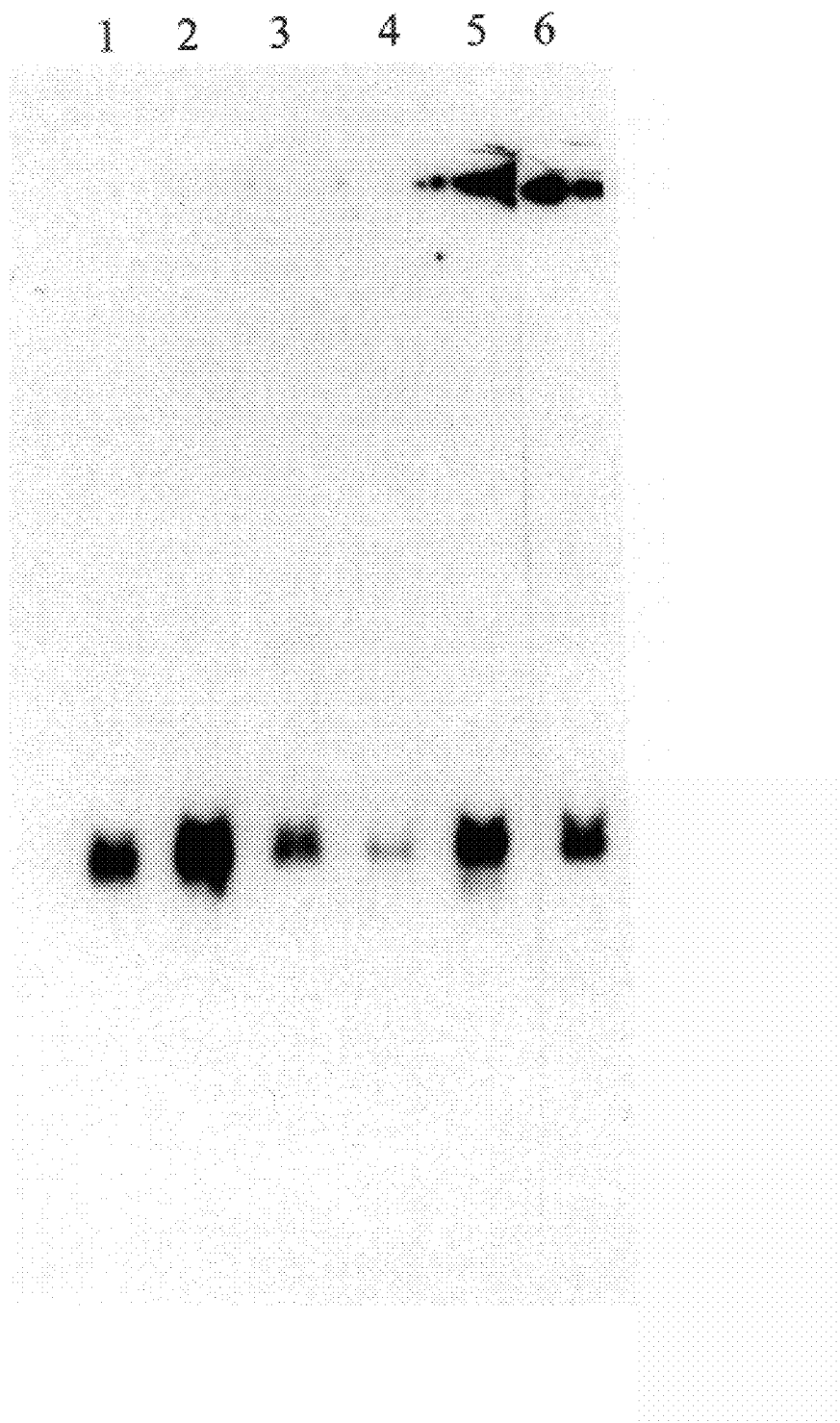

As shown in FIG. 3, all of pZeoSV1C9-introduced clones (lanes 4–6: P3, P8, P9) and pZeoSVγ9-introduced clones (lanes 1–3: N4, N7, N8) produce mRNA encoding the introduced single-chain antibody. There was no detectable difference between any clones in amount of mRNA encoding the single-chain antibody.

Figure 4:
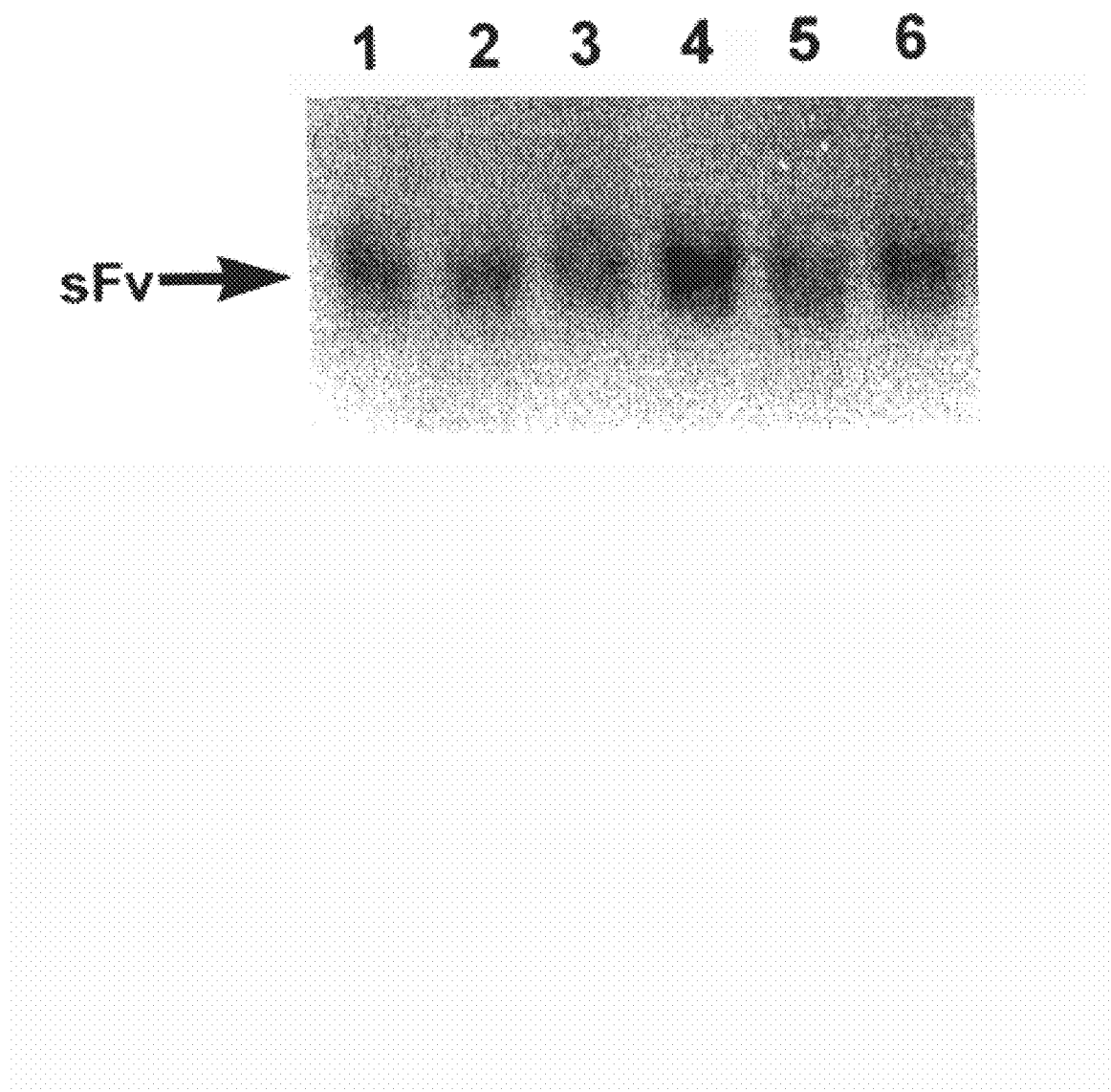

In addition, the results of similar procedures carried out on other clones exhibiting resistance against Zeocin are shown in FIG. 4. In FIG. 4, lanes 1–4 indicate the results for pZeoSV1C9-introduced clones P9, P12-2, P10, and P20, respectively, and lanes 5 and 6 indicate the results for pZeoSVγ9-introduced clones N4 and N8, respectively. Similarly to the above results shown in FIG. 3, all of clones produced mRNA derived from the introduced single-chain antibody gene, and there was no detectable difference between any clones in amount of mRNA derived from the single-chain antibody gene.

EXAMPLE 7

Analysis of RNA and DNA of Hepatitis B Virus from Transformed Cells

Into 6-cm dishes or 6-well plates for tissue culture, single-chain antibody-expressing transformed cells (pZeoSV1C9-introduced HB611 cells and pZeoSVγ9-introduced HB611 cells) were plated, and RNA and DNA were recovered when the culture became confluent.

Figure 5:
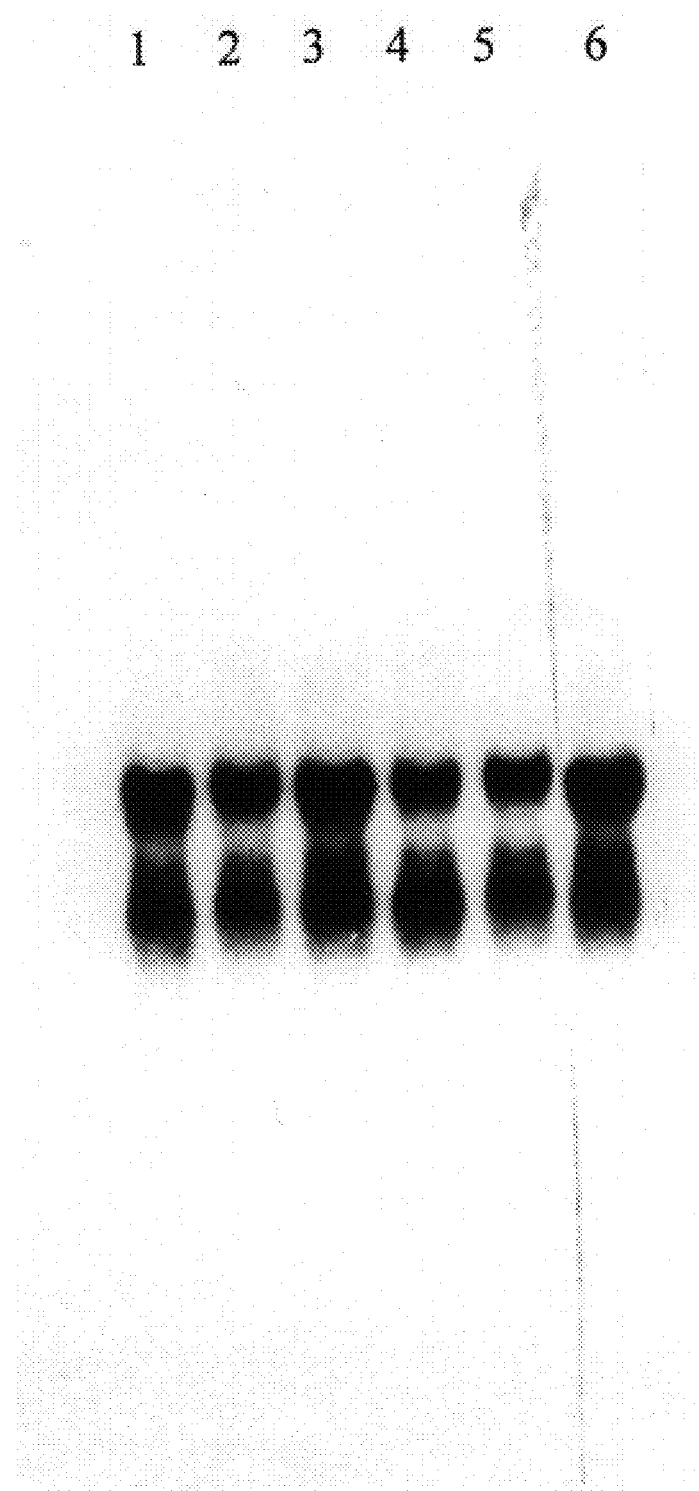

The recovery of RNA was conducted by the method described in Example 1, and the analysis was conducted by the method described in Example 6. In the analysis, the amount of RNA of HBV was studied by Northern blot analysis using, as a probe, HBV DNA (GenBank Accession No. X01587) labeled with $^{32}P$ using Rediprime™ (Amersham). As a result, all of HB611 transformed cells carrying pZeoSV1C9 (lanes 4–6; P3, P8, and P9, respectively) and pZeoSVγ9 (lanes 1–3; N4, N7, and N8, respectively) showed similar expression of hepatitis B virus mRNA (FIG. 5).

Figure 6:
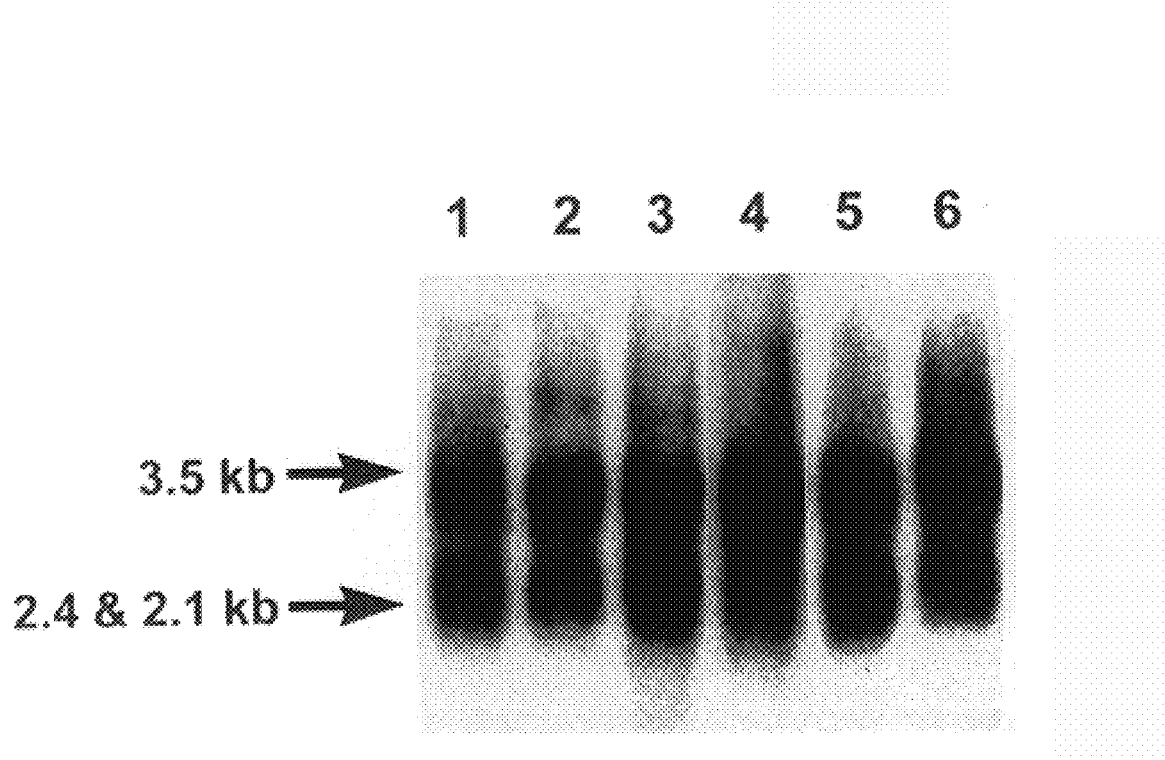
FIG. 6 is a photograph of electrophoretic gel indicating the result of the same analysis as in FIG. 5 conducted on other clones. Lanes 1–4: RNAs derived from clones (P9, P12-1, P10, and P20) obtained by introducing pZeoSV1C9; lanes 5 and 6: RNAs derived from clones (N4 and N8) obtained by introducing pZeoSVγ9.

In addition, the results of similar procedures carried out using other clones are shown in FIG. 6. In FIG. 6, lanes 1–4 indicate the results for P9, P12-2, P10, and P20, respectively, and lanes 5 and 6 indicate the results for N4 and N8, respectively. Similarly to the above results shown in FIG. 5, all of clones showed similar expression of hepatitis B virus mRNA.

Extraction of DNA was conducted as follows. In 6-well dishes, after washing each well with 3 mL of PBS, 1 mL of lysis buffer (10 mM Tris-HCl, pH 7.5, 10 mM EDTA, 1% SDS) was added, and the cells were recovered using a cell scraper. One-hundredth volume of proteinase K (20 mg/mL) was then added, incubated overnight at 37° C., and one-hundredth volume of RNase A (10 mg/mL) was further added, followed by incubation at 37° C. for 2 hours. From the cells subjected to the above treatments, DNA was extracted using phenol/chloroform/isoamyl alcohol, and then precipitated by adding one-tenth volume of 3 M sodium acetate and two volumes of ethanol. After washing with 70% ethanol, the precipitate was dissolved in TE solution (10 mM Tris-HCl, pH 8.0, 0.1 mM EDTA) to yield a DNA solution.

The DNA thus prepared was cleaved by incubating it with restriction enzyme Hind III for 4 hours at 37° C. After extraction using phenol/chloroform/isoamyl alcohol, precipitation with ethanol, and washing with 70% ethanol as described above, the cleaved DNA was dissolved in TE solution, and analyzed by Southern blotting using Hybond $N^+$ filters (Amersham) to study the amount of DNA replicative intermediates of HBV in the transformed cells. Hybridization conditions were in accordance with the protocol provided by Amersham. As a probe, the same one as that used in the above Northern blot analysis was used.

In result, as shown in FIG. 7, there was no remarkable difference in amount of HBV DNA integrated into the host chromosome detected in pZeoSV1C9-introduced HB611 cells (lanes 8 and 9: P3, lanes 10 and 11: P8, lanes 12 and 13: P9) and pZeoSVγ9-introduced HB611 cells (lanes 2 and 3: N4, lanes 4 and 5: N7, lanes 6 and 7: N8), as demonstrated by the similar density of the bands, confirming that in all cases, almost the same copy number of hepatitis B virus gene existed in the host chromosome DNA (the position of band "I" in FIG. 7).

However, as shown at the positions of bands "$D_1$ (linear double-stranded DNA)" and "S (single-stranded DNA)" in FIG. 7, the amount of the replicative intermediates of HBV was significantly reduced in pZeoSV1C9-introduced cells (lanes 8–13) when compared to pZeoSVγ9-introduced cells (lanes 2–7), indicating that the single-chain antibody of the present invention which contains the variable region of an anti-hepatitis B virus core protein mouse antibody as its principal component has an effect inhibiting DNA replication of hepatitis B virus, that is, an effect inhibiting propagation of hepatitis B virus.

In addition, the results of similar procedures carried out using other clones are shown in FIG. 8. In FIG. 8, lanes 2–5 indicate the results for P9, P12-2, P10, and P20, respectively, and lanes 6 and 7 indicate the results for N4 and N8, respectively.

Similarly to the above results, although there was no difference in amount of HBV DNA integrated into the host chromosome between pZeoSV1C9-introduced clones and pZeoSVγ9-introduced clones (band I in FIG. 8), the amount of the replicative intermediates of HBV was significantly reduced in pZeoSV1C9-introduced clones when compared to pZeoSVγ9-introduced clones (band D2, D1, and S in FIG. 8, wherein D2 corresponds to circular double-stranded DNA), indicating the same results as in FIG. 7 described above.

EXAMPLE 8

Analysis of Production of Single-chain Antibody Protein in Transformed Cells

From a pZeoSV1C9-introduced HB611 clone (P12-2) and a pZeoSVγ9-introduced HB611 clone (N8), cell lysates were prepared using lysis buffer (50 mM Tris-HCl, pH 7.5, 10 mM EDTA, 0.5% Triton X-100, 1 μg/ml aprotinin, 1 μg/ml leupeptin, 100 μg/ml PMSF, 1 μg/ml pepstatin A). Five μg of the lysate (100 μg protein/1 ml buffer) was precleaned with 10 μg of normal rabbit IgG (Dako), and then subjected to an antigen-antibody reaction with 5 μg of anti-HBV core protein rabbit antibody (Dako) or normal rabbit IgG antibody (Dako). The products from the above antigen-antibody reaction was then recovered by immunoprecipitation using 25 μl of protein G-Sepharose 4FF (Pharmacia) having the property of being bound by IgG. The recovered material was subjected to SDS-polyacrylamide gel electrophoresis, and Western blotting was conducted using an antibody against E-tag added to the C-terminus of the sFv. As a result, as shown in FIG. 9, only when the lysate from P12-2 was used and immunoprecipitation was conducted with anti-HBV core protein rabbit antibody (lane 4), a single band of about 30 kDa could be detected. This result confirms that in the transformed cell (P12-2) into which a gene for a single-chain antibody against HBV core protein was introduced and in which replication of HBV was suppressed, the single-chain antibody was intracellularly produced, and it formed a complex with HBV core protein.

EXAMPLE 9

Effect of Single-chain Antibody on Proliferation of HB611

In order to confirm that the suppressive effect on HBV replication by the single-chain antibody shown in FIGS. 7 and 8 does not result from inhibition of cell proliferation due to production of the single-chain antibody, proliferation of pZeoSV1C9-introduced HB611 clones and pZeoSVγ9-introduced HB611 clones were studied using MTT assay (3-[4,5-dimethylthiazol-2-yl]-2,5-diphenyltetrazolium bromide, MTT, Sigma).

Average values ±SD determined for pZeoSV1C9-introduced HB611 clones (6 clones) and pZeoSVγ9-introduced HB611 clones (3 clones) are shown in FIG. 10. In FIG. 10, ● indicates the result for pZeoSV1C9-introduced HB611 clones, and ■ indicates the result for pZeoSVγ9-introduced HB611 clones. As shown in FIG. 10, there was no difference in proliferation between these transformed cells until 180 hours after the start of measurement. It was thus demonstrated that the single-chain antibody against HBV core protein directly suppress HBV replication by forming a complex with HBV core protein without causing inhibition of proliferation of the host cells.

EXAMPLE 10

Preparation of Recombinant Cosmid Vector

A cosmid vector was prepared using an ca. 1.1 kb DNA fragment of 1C9 gene encoding a single-chain antibody against HBV core protein, extending from the EcoR I cleavage site located at 57 base pair upstream from the start codon ATG to the EcoR I cleavage site located at 114 base pair downstream from the stop codon TAG. In addition, for the γ9 gene having no activity as a single-chain antibody against HBV core protein, another cosmid vector was similarly prepared using an ca. 1.1 kb EcoR I fragment. Specifically, after the above-described blunt-ended ca. 1.1 kb EcoR I fragment was ligated to pAx1CAwt cosmid vector cleaved with Swa I, cosmid vectors containing no inserted fragments were digested with Swa I, and an aliquot of the reaction liquid was in-vitro packaged. After infection of *E. coli*. DH5α, cosmid DNA was recovered from emerged colonies, and analyzed on 1% agarose gel electrophoresis following cleavage with Hind III/Xba I. As a result, 4 clones in which the 1C9 gene has been inserted in the correct direction and 3 clones in which the γ9 gene has been inserted in the correct direction were obtained. From these clones, three clones were selected for each gene, and cleaved by Hind III/Xba I or Spe I/Nhe I. It was confirmed for each clone that the desired DNA fragment has been inserted in the correct direction, by detecting about 1 kb fragment after Hind III and Xba I digestion, or by detecting about 1.7 kb and about 1.1 kb fragments after Nhe I and Spe I digestion. The results of the confirmation using restriction enzymes are shown in FIG. 11.

EXAMPLE 11

Preparation of Recombinant Adenovirus

In order to prepare a recombinant adenoviral vector in which an expression unit of the above 1C9 or γ9 has been inserted into the site of E1 gene deletion in a human adenovirus type 5-derived replication defective recombinant-adenoviral vector (lacking E1 and E3 genes), the following procedures were carried out. In this example, the CAG promoter disclosed in the Japanese Patent Publication Kokai No. H3-168087 (1991) was used as a high expression promoter, and the recombinant adenoviral vectors were prepared according to an existing method (Miyake et al., *Proc. Natl. Acad. Sci.*, Vol. 93, 1320–1324 (1996); and the Japanese Patent Publication Kokai No. H7-298877 (1995)).

Starting from Ax1CAwt, a recombinant adenoviral vector in which only the CAG promoter has been inserted into the site of adenoviral E1 gene deletion (Kanegae et al., *Nucleic Acid Res.*, 23, 3816–3821, 1996), the viral DNA-terminal protein complex was prepared according to the existing method (the Japanese Patent Publication H7-298877 (1995)), and simultaneously digested with restriction enzymes EcoT22 I and Cla I. Using this restricted viral DNA-terminal protein complex and the cosmid vector prepared in Example 10 into which the single-chain antibody 1C9 gene or the single-chain antibody γ9 gene has been inserted, 293 cells were transformed by the calcium phosphate co-precipitation method. After cloning the produced recombinant adenoviruses, a desired virus was selected by restriction enzyme digestion (Xho I) of the viral DNAs. When digested with Xho I, the parent virus yields a 4.8 Kb DNA fragment, whereas the desired clone yields a 5.9 Kb DNA fragment. The results of restriction enzyme digestion of viral DNA are shown in FIG. 12. Based on analysis of the results, 2 recombinant adenoviral vectors expressing the 1C9 gene and 9 recombinant adenoviral vectors expressing the γ9 gene were obtained.

By using a recombinant adenoviral vector expressing the 1C9 gene as an agent for gene therapy, propagation of hepatitis B virus can be suppressed.

INDUSTRIAL APPLICABILITY

DNA of the present invention encodes an anti-hepatitis B virus core protein single-chain antibody, and when expressed intracellularly, the single-chain antibody can inhibit DNA synthesis hepatitis B virus, and thereby suppress propagation of hepatitis B virus. In addition, the anti-core protein single-chain antibody of the present invention may be expected to have an excellent effect even in pre-core mutant viral cases in which a therapy by enhancing the host immunity with the aim of excluding the virus may hardly be effective, because the target of the present antibody is the core protein antigen.

What is claimed is:

1. An isolated nucleic acid molecule comprising a polynucleotide having a nucleotide sequence selected from the group consisting of:
   (a) a nucleotide sequence of SEQ ID NO: 1; and
   (b) a nucleotide sequence encoding the amino acid sequence of SEQ ID NO: 2.

2. An isolated nucleic acid molecule comprising a polynucleotide that specifically hybridizes to:
   (a) an antisense strand of SEQ ID NO: 1 under conditions of a hybridization buffer comprising 50% formamide and 5×SSC at 42° C., or
   (b) an antisense strand of a polynucleotide that encodes a polypeptide comprising the amino acid sequence of SEQ ID NO: 2 under conditions of a hybridization buffer comprising 50% formamide and 5×SSC at 42° C.,
   wherein said isolated nucleic acid encodes a polypeptide that specifically binds to hepatitis B virus core protein.

3. A vector comprising the nucleic acid molecule of claim 1 or 2.

4. The vector of claim 3 that is an adenoviral vector.

5. A host cell comprising the vector of claim 3.

6. A process for producing a recombinant polypeptide comprising the steps of:
   (a) culturing the host cell of claim 5 under conditions sufficient for the production of said polypeptide, and
   (b) recovering said polypeptide.

* * * * *